United States Patent [19]

Vogel et al.

[11] Patent Number: 5,409,900
[45] Date of Patent: Apr. 25, 1995

[54] PORPHYCENE COMPOUNDS FOR PHOTODYNAMIC THERAPY

[75] Inventors: Emanuel Vogel, Cologne; Clemens Richert, Munich; Thomas Benninghaus; Martin Müller, both of Cologne, all of Germany; Alexander D. Cross, Atherton, Calif.

[73] Assignee: Cytopharm, Inc., Menlo Park, Calif.

[21] Appl. No.: 102,772

[22] Filed: Aug. 6, 1993

Related U.S. Application Data

[62] Division of Ser. No. 875,314, Apr. 29, 1992, Pat. No. 5,262,401, which is a division of Ser. No. 723,394, Jun. 28, 1991, Pat. No. 5,179,120.

[51] Int. Cl.[6] .................. A61K 31/40; C07D 487/22
[52] U.S. Cl. ..................................... 514/17; 514/410; 514/2; 514/18; 540/472; 530/329; 530/330; 530/331; 530/345
[58] Field of Search ............... 540/472; 514/2, 32, 514/410, 17, 18; 424/9, 11

[56] References Cited

U.S. PATENT DOCUMENTS

| | | | |
|---|---|---|---|
| 5,015,478 | 5/1991 | Jori et al. | 540/472 |
| 5,132,101 | 7/1992 | Vogel et al. | 604/20 |
| 5,179,120 | 1/1993 | Vogel et al. | 514/410 |
| 5,262,401 | 11/1993 | Vogel et al. | 540/472 |

*Primary Examiner*—Mukund J. Shah
*Assistant Examiner*—Pavanaram K. Sripada
*Attorney, Agent, or Firm*—Oblon, Spivak, McClelland, Maier & Neustadt

[57] ABSTRACT

A porphycene having the structure

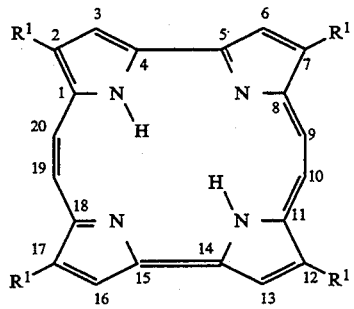

wherein each $R^1$ is, independently, (a) —$(CH_2)_n$—X, where n=1–4, X is $OR^2$ and $R^2$ is $C_{1-6}$ alkyl, aralkyl or aryl; CN; OH; $OSO_2R^2$; $NH_2$; $NHR^2$; $NR_2^2$; SH; $SR^2$; $S(O)_{1-2}R^2$; COOH; $CO_2R^2$; $C(O)NH_2$; $C(O)NHR^2$; $C(O)NR_2^2$; halogen; or CHO;

(b) —$(CH_2)_m CH=CH_2$ where m is 0–2; or (c) —$(CH_2)_n$—O—G where G is a mono- or oligosaccharide;

(d) —$(CH_2)_{2n}$—X, where X is an amino acid, oligopeptide covalently bonded by an ether-, ester- or amine-bond or —Y— $(CH_2)_n$-porphycene[2] (porphycene[2] being a compound of the same structure and Y is a direct bond; —O—; or —CH=$CH_2$); or (e) where one, two or three of the substituents $R^1$ are $C_{1-6}$ alkyl or aryl and the remaining substituents are as above under (a)–(d), and salts and metal complexes thereof. The porphycene compounds and pharmaceutical compositions containing the compounds are useful in photodynamic therapy treatment of tumors and psoriasis.

15 Claims, 4 Drawing Sheets

PORPHYCENE COMPOUNDS FOR PHOTODYNAMIC THERAPY

This is a division of application Ser. No. 07/875,314, U.S. Pat. No. 5,262,401 filed on Apr. 29, 1992, which is a division of application Ser. No. 07/723,394, U.S. Pat. No. 5,179,120 filed on Jun. 28, 1991.

BACKGROUND OF THE INVENTION

1. Field of the Invention

The invention relates to novel porphycene compounds and pharmaceutical compositions containing these compounds which are useful for therapeutic treatment.

2. Discussion of the Background

During the past few years there has developed a widespread recognition that modern, though sophisticated, cancer diagnosis and treatments have served neither to reduce overall the number of cases of reported cancers in the U.S.A. nor, save the notable cases, the death rate. This is a disheartening result for the billions of dollars invested in conquering the disease. Moreover, surgery, radiotherapy and chemotherapy are all associated with major debilitating side effects such as trauma, severe immunosuppression or toxicity which are not easily surmounted by patients already compromised by ill-health.

Early work in the 1970's, followed by rapidly expanding studies in the 1980's, has shown that photodynamic therapy (PDT) offers a viable, less toxic and generally less painful avenue to treatment of cancer. Not all cancers are candidates for PDT. However, neoplasms of hollow organs and skin, including multifocal carcinoma in situ, sometimes inoperable, and with no good track record for treatment by established therapeutic procedures, appear to be targets for PDT.

In photodynamic therapy, porphyrinoid dyes are administered to a patient and localize in neoplastic tissues (Lipson et al, J. Thoracic Cardiovascular Surgery, 1961, 42:623–629). Irradiation of the porphyrinoid dye with light - at a wavelength which corresponds to an absorption band of the dye results in destruction of the neoplastic tissue. See also Kessel, D., "Methods in Porphyrin Photosensitization" Plenum Press, New York, 1985; Gomer, C. J., "Photodynamic Therapy", Petgammon Press, Oxford, 1987 and Doiron, D. R. and Gomer, C. J., "Porphyrin Localization and Treatment of Tumors", Liss, New York, 1984. The use of a fiber optic laser light source is described in U.S. Pat. No. 4,957,481.

Dougherty et al (Cancer Res., 1978, 38:2628; Photochem. Photobiol, 1987, 45:879) pioneered the field with infusion of photoactivatable dyes, followed by appropriate long wavelength radiation of the tumors (600+ nm) to generate a lethal shortlived species of oxygen which destroyed the neoplastic cells. Early experiments utilized a mixture termed hematoporphyrin derivative (HPD). See also Lipson et al, J.N.C.I., 1961, 26:1; Dougherty et al, J.N.C.I., 1975, 55:115; Diamond et al, Lancet, 1972(II), 1175; D. Dolphin, "The Porphyrins", vol I, Academic Press, New York, 1978; and D. Kessel, Photochem. PhotoBiol., 1984, 39:851. The deficiencies of HPD, especially prolonged phototoxicity caused by retained HPD components in human skin led to its displacement by a purified fraction termed dihematoporphyrin ether (DHE) which, although yielding improvements over HPD, nevertheless still suffered certain practical limitations. Relatively weak absorption in the wavelength range above 600 nm, retention in dermal cells (potentially leading to phototoxicity), only modest or low selectivity for tumor cells versus other cell types in vital organs, the inability to use available, modern, inexpensive diode lasers, and uncertain chemical constitution of the mixtures are all known negative features of DHE and HPD. The great majority of the earlier PDT agents studied have been derived from natural sources (porphyrins, chlorins, purpurins, etc.) or from known chemicals originating in the dyestuffs industry (e.g., cyanine dyes). For more recent PDT agents derived from natural sources see U.S. Pat. No. 4,961,920 and U.S. Pat. No. 4,861,876.

In animal and cell culture experiments one observes, following PDT, depending on the incubation time, damage to the vasculature, cell membranes, mitochondria and specific enzymes. When absorbed in tumor cells, an increased selectivity can be obtained by injecting the porphyrinoid sensitizers enclosed in liposomes (Ricchelli and Jori, Photochem. Photobiol., 1986, 44:151). Porphyrinoid dyes can be transported in the blood with the aid of lipoproteins such as low-density lipoprotein (Jori et al, Cancer Lett., 1984, 24:291).

PDT has been used to treat bladder, bronchial, bone marrow and skin tumors (Dougherty, Photochem. Photobiol., 1987, 45:879, Sieber et al, Leukemia Res., 1987, 11:43) as well as severe psoriasis (Diezel et al, Dermatol. Monatsschr., 1980, 166:793; Emtenstam et al, Lancet, 1989 (I), 1231). Treatment of viruses in transfused blood has also been reported (Matthews et al, Transfusion, 1988, 28:81; Sieber et al, Semin. Hematol., 1989, 26:35).

As the deficiencies of earlier PDT agents have become apparent, it also becomes possible to define activity parameters for improved chemically pure photoactivatable dyes for PDT therapy, available by chemical synthesis. Moreover, the products of synthesis lend themselves more readily to further chemical structural manipulation than do the naturally occurring starting materials which can be expensive and bear chemically sensitive constituents. The synthesis of novel porphycene macrocycles embracing four pyrrole rings has been described by Vogel and coworkers. Alkylated porphycenes have also been prepared (R=Me, Et, n-Pr, n-octyl, phenyl) and the photochemical properties determined. The suitability of these compounds for PDT was noted and confirmed in animal studies (Guardiano et al, Cancer Letters, 1989, 44, 1).

Synthetic efforts have focused on porphryinoid compounds which are highly absorptive in the longer wavelength range of about 600–1200 nm, where the transparency of tissue is higher. Compounds such as purpurines (Morgan et al, J. Org. Chem., 1986, 51:1347; Morgan et al, Cancer Res., 1987, 47:496; Morgan et al, J. Med. Chem., 1989, 32:904; Hoober et al, Photochem. Photobiol., 1988, 48:579), naphthocyanin silicon complexes (Firey et al, J. Am. Chem. Soc., 1988, 110:7626), chlorins (Robert et al, J.N.C.I., 1988, 80:330; Kessel, Cancer Res., 1986, 46:2248), bacteriochlorins (Beams et al, Photochem. Photobiol., 1987, 46:639) and substituted phenylporphyrins (Kreimer-Birnbaum, Semin. Hematol., 1989, 26:157) have been prepared and tested in vivo. Additional PDT agents are described in EP 276,121.

Pyrrole-containing ring systems larger than porphycene have also been prepared and evaluated as photosensitizers. Sessler et al have prepared and studied texaphyrin (J. Am. Chem. Soc., 1988, 110:5586) and Woodward et al and Johnson et al have prepared and investigated the sapphyrin ring system. Additionally, the platyrin system has been studied by LeGoff (Tetrahedron, Lett., 1978, 4225; J. Org. Chem., 1987, 710) and vinylogous porphyrins have been studied by Franck (Angew. Chem., 1986, 98:1107; Angew. Chem. Int. Ed. Eng., 1986, 25:1100; Angew. Chem., 1988, 100:1203; Angew. Chem. Int. Ed. Eng., 1988, 27:1170).

A need continues to exist, therefore, for new compounds for use in PDT therapy, which compounds are easily available, have low intrinsic toxicity, are efficient photosensitizers for singlet oxygen production, have selective uptake in rapidly proliferating cells, are rapidly or at least moderately rapidly degraded and eliminated from the tissues after administration and which are available as chemically pure and stable compounds easily subject to synthetic modification. The compound should penetrate tissue quickly, especially if used for topical application.

SUMMARY OF THE INVENTION

Accordingly, one object of the present invention is to provide new and effective compounds for use in photodynamic therapy whose properties and characteristics approach the ideal characteristics of PDT dyes listed above.

This and other objects which will become apparent from the following specification have now been achieved with the compounds of the present invention. The present compounds have utility as PDT dyes for use in cancer therapy and dermatological diseases, blood purification (elimination of viruses and bacteria, e.g., CMV, HIV), etc.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing, wherein.

DETAILED DESCRIPTION OF THE PREFERRED EMBODIMENTS

Figure 1:
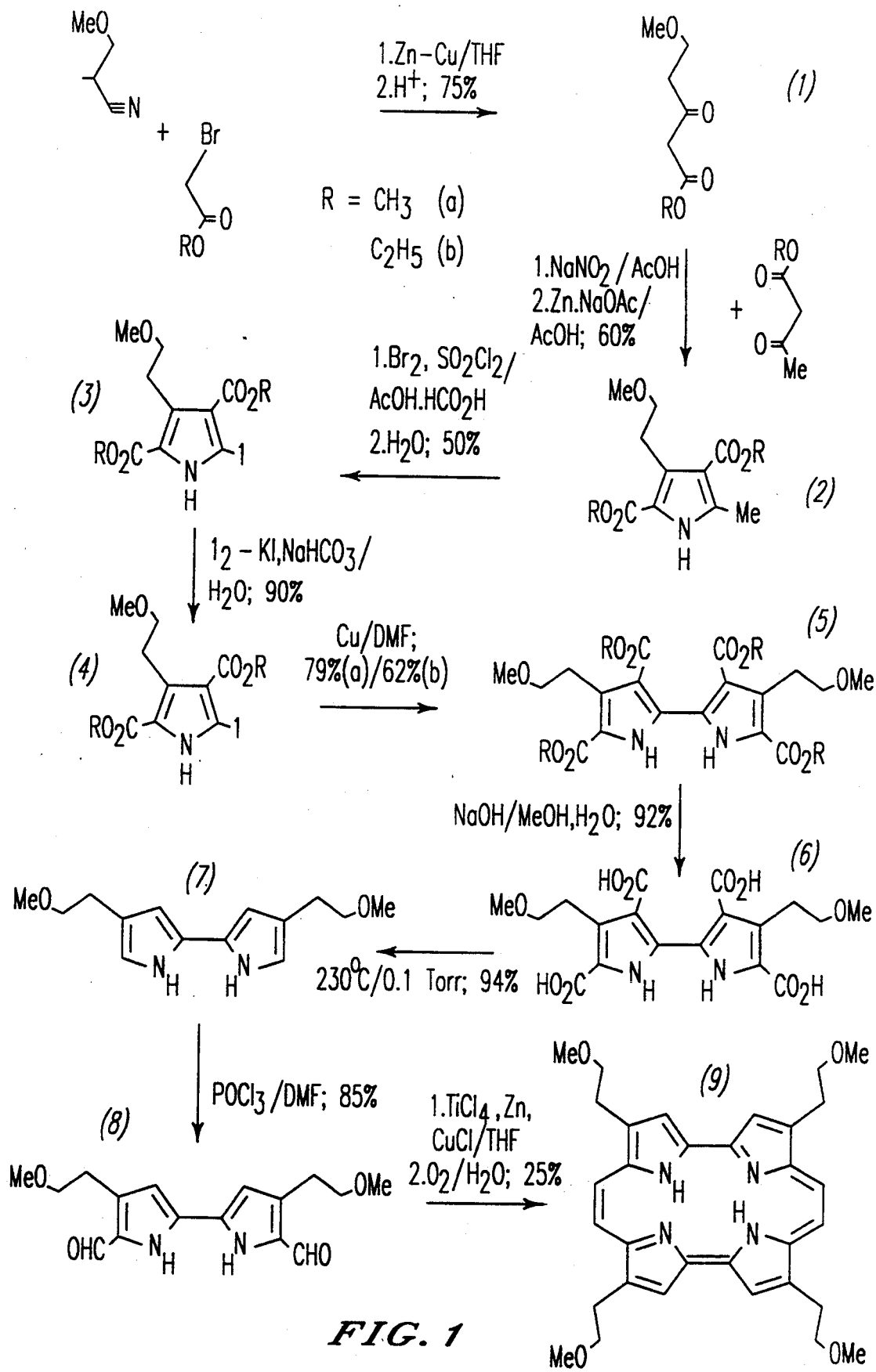
FIG. 1 illustrates a synthesis of the tetrakis(alkoxyalkyl)porphycene compounds of the present invention, specifically tetrakis(methoxyethyl)porphycene.

The porphycene compounds of the present invention have the structure shown below:

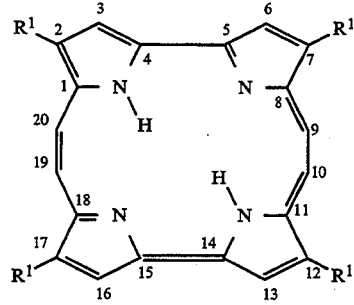

where each $R^1$ in the 2, 7, 12 and 17-positions of the porphycene structure is, independently of one another, (a) the group —$(CH_2)_n$—X, where n=1–4, X is $OR^2$ and $R^2$ is $C_{1-6}$ alkyl, aralkyl or aryl; or X is CN; OH; $OCOR^2$; $OSO_2R^2$; $NH_2$; $NHR^2$; $NR_2^2$; SH; $SR^2$; $S(O)_{1-2}R^2$; COOH; $C(O)NH_2$, $C(O)NHR^2$, $C(O)NR_2^2$, $CO_2R^2$ halogen or CHO; (b) the group —$(CH_2)_m$—CH=$CH_2$ where m=0–2 or (c) the group —$(CH_2)_n$—O—G where G is a mono- or oligosaccharide covalently bonded to the porphycene or (d) the group —$(CH_2)_n$—X where X is an amino acid, oligopeptide covalently bonded by an ether-, ester- or amine-bond or $Y(CH_2)_n$-porphycene$^2$ (porphycene$^2$ being a compound of the same structure and Y is a direct bond; —O—; or —CH=CH—) or (e) where one, two or three of the substituents $R^1$ are $C_{1-6}$ alkyl or aryl and the remaining substituents are as described above under (a)–(d), salts and metal complexes thereof. For all four substituents $R^1$=alkyl, see U.S. Pat. No. 4,913,907.

Suitable aryl groups include $C_{6-20}$ carbocyclic aryl groups, optionally substituted with one or more $C_{1-6}$ alkyl groups. Examples include phenyl, naphthyl, indanyl etc. Suitable aralkyl groups are the aryl groups defined above bonded to a $C_{1-6}$ alkylene grop. Examples include benzyl, phenylethyl, phenylpropyl, phenylbutyl, etc.

Each amino acid may have either the D or L form. Preferred oligopeptides will have 2–6 amino acid residues, more preferably 2–3 residues. It is convenient to use the 20 naturally occurring amino acids.

The oligosaccharide covalently bonded to the porphycene may have 2–6, preferably 2–3 saccharide units. Both pentose and hexose saccharides may be used, including, but not limited to, glucose, mannose, galactose and fructose.

Preferred compounds are those in which at least one $R^1$ is —$(CH_2)_n$—X where X is $OR^2$, OH, $OCOR^2$, $OSO_2R^2$ or halogen (I, Br, Cl), and compounds in which $R^1$ is —$(CH_2)_m$—CH=$CH_2$. Especially preferred are compounds in which at least one $R^1$ is —$(CH_2)_2$—X where X is $OCH_3$, OH, bromine and compounds in which $R^1$ is —$(CH_2)_n$—O—G, where G is a pentose or hexose.

The compounds of the present invention may be prepared by coupling appropriately substituted dialdehydes to form the porphycene ring structure as is shown below.

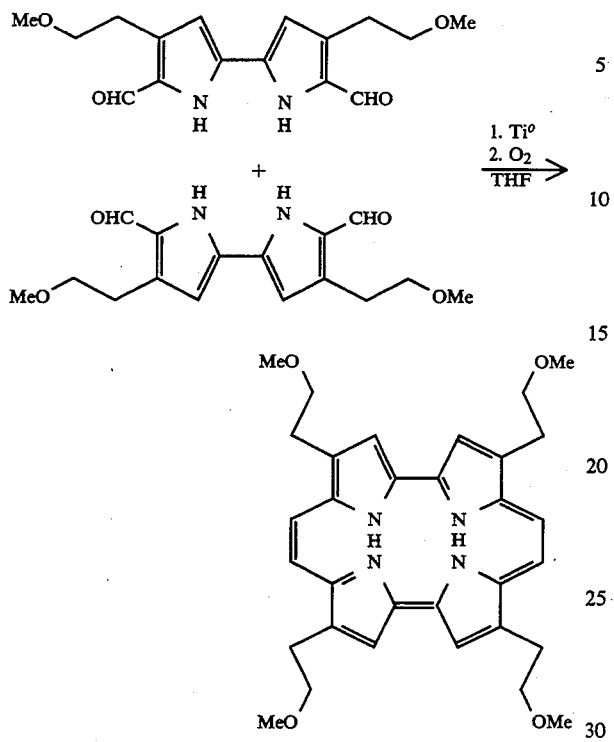

Porphycenes with two different substituents in the 2,7- and 12,17-positions are readily obtained by mixed coupling of two different dialdehydes as is shown below for the case of 2,7-bis(methoxyethyl)-12,17-di-n-propylporphycene.

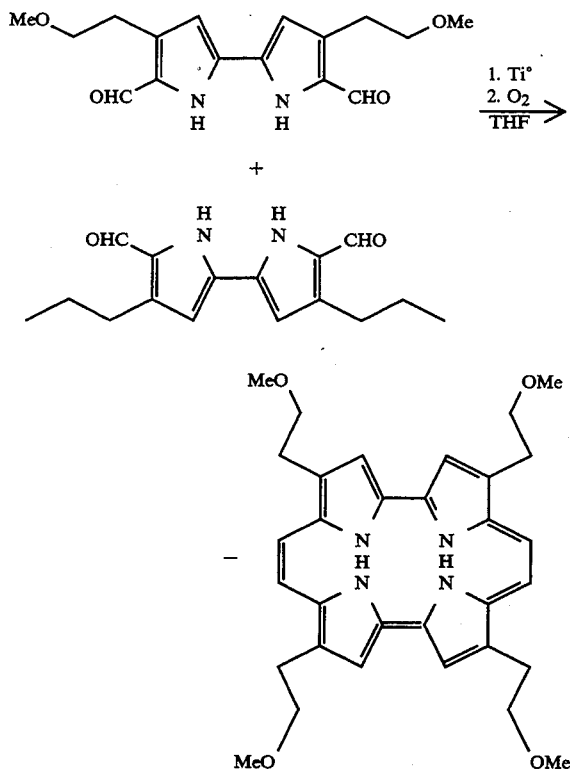

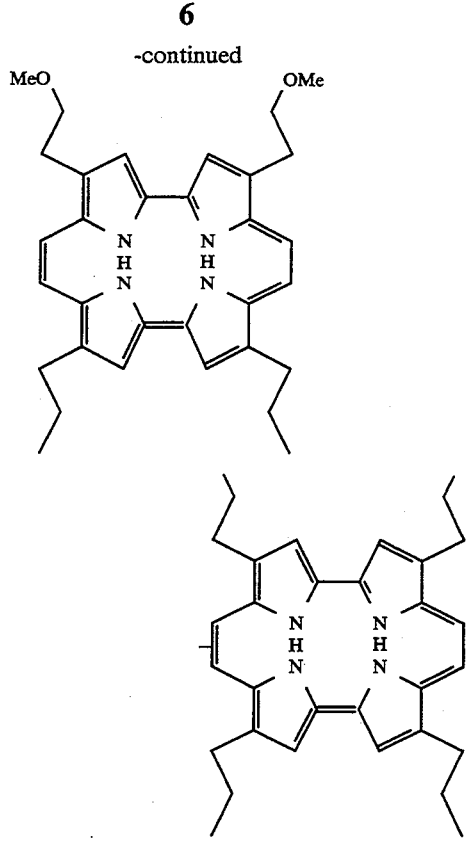

The coupling of the dialdehyde components may be accomplished with a McMurry reaction utilizing low valency titanium in a non-reactive solvent. See for example McMurry and Fleming, J. Am. Chem. Soc., 1974, 96:4708; McMurry, Chem. Rev., 1989, 89:1513; Lenoir, Synthesis, 1989, 883; Mukaiyama et al, Chem. Lett., 1973, 1041. Typically, reductive coupling is carried out using a titanium amalgam prepared by reacting titanium tetrachloride with an additional metal such as zinc, copper, aluminum and salts thereof. The reductive coupling reaction is carried out in a non-reactive solvent such as a hydrocarbon or ether solvent. Typical solvents include alkanes having from 5–10 carbon atoms such as pentane, hexane, heptane, etc., as well as ether solvents such as diethyl ether, crown ethers, glyme and tetrahydrofuran (THF). If desired, the coupling reaction can be heated to facilitate the reaction, i.e., the reaction can be conducted under reflux conditions. The dialdehyde components to gain the bis(alkoxyalkyl)-dialkylporphycenes, are on one hand those described below and, on the other hand, well known dialdehydes, preferred in the present invention, such as 5,5'-diformyl-4,4'-di-n-propyl-bipyrrole (e.g., E.Vogel et al; Angew. Chem. Int. Ed. Engl. 26 (1987)928).

Synthesis of compounds in which $R^1$ is $-(CH_2)_n-X$ where X is $OR^2$ represent a convenient starting synthesis for the compounds of the present invention. With an appropriate cyano ether, it is possible to synthesize the dialdehyde coupling components which ultimately provide the porphycene ring structure. Beginning with cyano ethers having the structure $R^2O-(CH_2)_n-CN$ where $R^2$ is $C_{1-6}$ alkyl and n is 1–4, one can systematically construct the dialdehyde coupling components required to prepare the porphycene derivatives in which $R^1$ is $-(CH_2)_n-OR^2$. FIG. 1 illustrates a synthesis of tetrakis(methoxyethyl)-porphycene starting from the cyano ether in which $R^2$ is $CH_3$ and $n=2$. The remaining porphycene compounds in which $R^1$ is $-(CH_2)_n-OR^2$ can be synthesized by an analogous synthetic procedure using the appropriate cyano ether. The cyano ethers may be purchased commercially or are available by cyano-dehalogenation displacement reactions on the corresponding halo-ether (Friedrich and Wallenfels, in Rappoport, "The Chemistry of the Cyano Group", pages 77–86, InterScience, New York, 1970). For example, tetrakis(ethoxyethyl)-porphycene, tetrakis(propoxyethyl)porphycene, tetrakis(butoxyethyl)porphycene, tetrakis(pentoxyethyl)porphycene and tetrakis(hexyloxyethyl)porphycene can be prepared from starting cyanoethers in which $n=2$ and $R^2$ is straight chain or branched ethyl, propyl, butyl, pentyl and hexyl. Similarly, tetrakis($C_{1-6}$ alkoxymethyl)porphycene, tetrakis($C_{1-6}$ alkoxypropyl)porphycene, tetrakis($C_{1-6}$ alkoxybutyl)porphycene, tetrakis($C_{1-6}$ alkoxypentyl)porphycene and tetrakis($C_{1-6}$ alkoxyhexyl)porphycene compounds can be prepared from the corresponding cyano ethers where $R^2$ is $C_{1-6}$ alkyl and n is 1, 3, 4, 5 or 6. A particularly preferred compound is tetrakis(methoxyethyl)porphycene. The bromoester which is condensed with the cyano ether in the first step shown in FIG. 1, is preferably a lower alkyl ($C_{1-6}$) bromo ester, more preferably a methyl or ethyl ester.

Reaction of the tetrakis(alkoxyalkyl)porphycene as its nickel or zinc complex, preferably the nickel complex, with about 0.7 moles of $BBr_3/B(OH)_3$ results in conversion of a single alkoxyalkyl group into the corresponding bromoalkyl group. Reaction of about 1.2 moles of $BBr_3/B(OH)_3$ results in the corresponding bis(bromoalkyl)porphycenatonickel complex, and reaction with 2 moles of $BBr_3/B(OH)_3$ gives the tris-product. The use of higher molar amounts of $BBr_3/B(OH)_3$ provides the tetrakis(bromoalkyl)porphycene compounds. The same products are obtained if solid boric acid is added to a solution of the substrate porphycene and boron tribromide is added subsequently.

Figure 2:
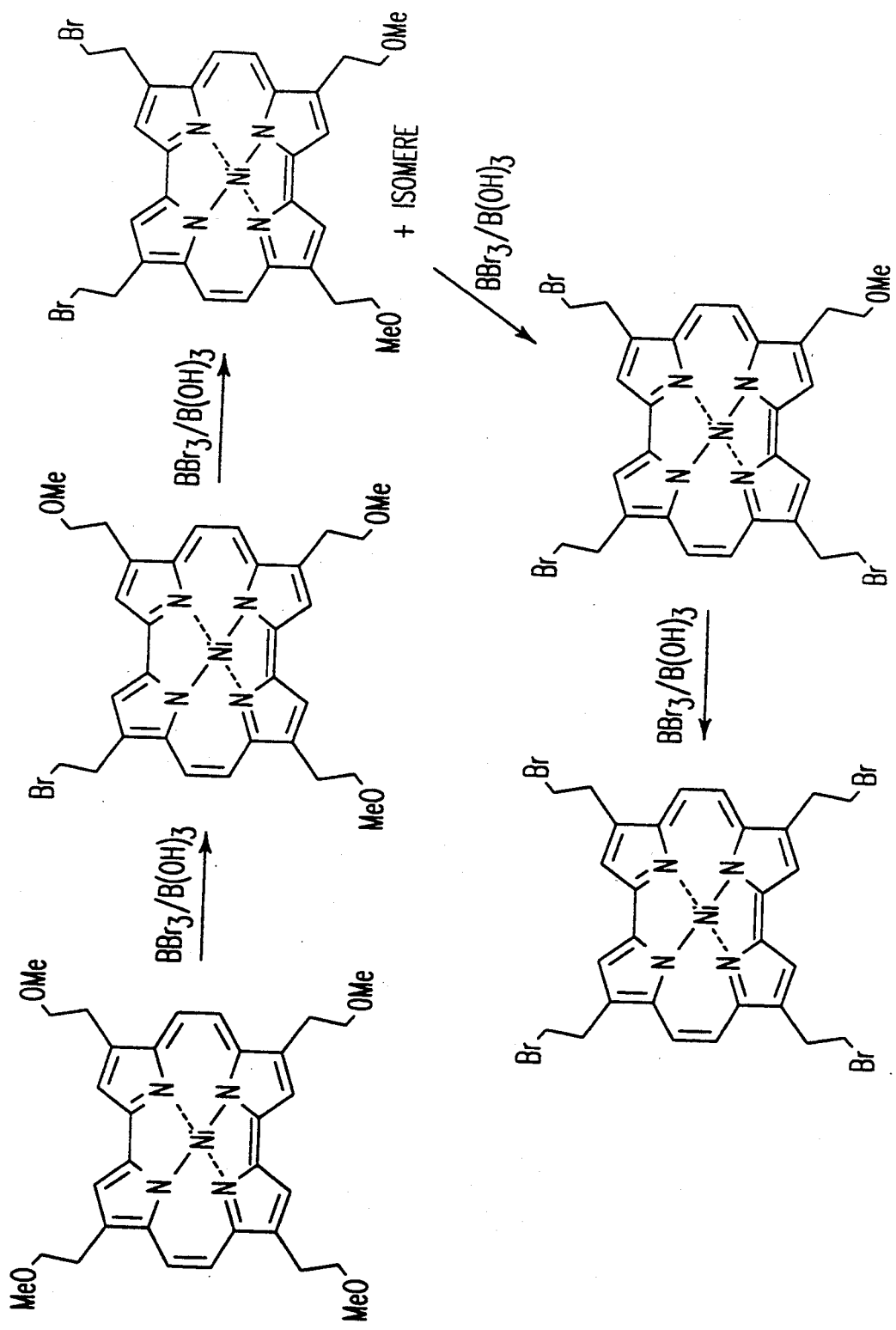
FIG. 2 illustrates the preparation of mono-, bis-, tris- and tetrakis(bromoalkyl)porphycenatonickel compounds which, following demetallation, provide compounds of the present invention.

The reaction is generally conducted at low temperatures, for example about $-40°$ to about $-120°$ C., preferably about $-78°$ C., and the reaction mixture then warmed to room temperature. The reaction is generally conducted in an inert organic solvent which can be readily removed by distillation or vacuum evaporation. Preferred solvents are halogenated hydrocarbons and a particularly preferred solvent is dichloromethane. Purification of the desired brominated porphycenatonickel complex is accomplished by conventional extraction and purification procedures. Preparation of the mono-, bis-, tris- and tetrakis(bromoalkyl)porphycenatonickel complex of a preferred embodiment of the present invention is shown in FIG. 2.

Metal complexes, preferably smaller metal complexes such as $Ni^{+2}$, $Zn^{+2}$, etc of the porphycene compounds of the present invention can be easily prepared by the addition of metal salts, e.g., metal acetates, to the porphycene compounds in acid medium, such as glacial acetic acid. Demetallation occurs when the metal complex is reacted with concentrated sulfuric acid at room temperature with stirring. Hydrogen ions displace the metal atom during the demetallation reaction (Buchler, J. W. in Smith, K. M. (Ed): "Porphyrins and Metalloporphyrins", Elsevier, Amsterdam, 1975; Buchler, J. W. in Dolphin, D. (Ed), "The Porphyrins," Vol. I, Academic Press, New York, 1978; Dorough et al, J. Am. Chem. Soc., 1951, 73:4315).

Reaction of the tetrakis(alkoxyalkyl)porphycene compounds with $BBr_3$ may also yield hydroxyalkyl porphycenes. By controlling the amount of boron tribromide reagent, it is possible to optimize the production of 1, 2, 3 or 4 hydroxyalkyl substituents ($R^1$ is $-(CH_2)_n-OH$), leaving the remaining alkoxyalkyl substituents intact. The synthesis of hydroxyalkyl substituents on the porphycene is possible if boric acid is omitted and the substrate is the uncomplexed porphycene.

The remaining compounds of the present invention are available synthetically by further reactions on any of the mono-, bis-, tris- or tetrakis (bromoalkyl)- or (hydroxyalkyl) porphycene compounds. Olefinic groups ($R'$ is $-(CH_2)_m-CH=CH_2$), such as vinyl groups, can be introduced into the porphycene compound by reaction of the appropriate bromoalkyl porphycene under dehydrohalogenation conditions. Loss of HBr results in the synthesis of mono-, bis-, tris- and tetrakis(vinyl)porphycene compounds from the corresponding mono-, bis-, tris- and tetrakis(bromoethyl)porphycene compounds ($n=2$). Analogously, a carbon-carbon double bond can be introduced into substituent $R^1$ by eliminating HBr from a substituent having the formula $-(CH_2)_n-Br$, where $n=3$ or 4. The dehydrohalogenation can be conducted under any suitable dehydrohalogenation conditions, generally through the addition of a base such as an alkoxide, amine or hydroxide base. For example, t-butoxide, diazobicycloundecene (DBU) or aqueous sodium hydroxide/pyridine may be used to dehydrohalogenate the bromoalkyl porphycene and thereby introduce a carbon-carbon double bond. Obviously, other dehydrohalogenation conditions not specifically disclosed are suitable for the dehydrohalogenation reaction so long as dehydrohalogenation is effected. A particularly preferred dehydrohalogenating reagent is DBU.

Through dehydrohalogenation, porphycene compounds in which $R^1$ is $-(CH_2)_m-CH=CH_2$ where m is 0, 1 or 2 can be prepared. The dehydrohalogenation reaction can be used to prepare porphycene compounds in which 1, 2, 3 or 4 of the $R^1$ substituents contain a carbon-carbon double bond by dehydrohalogenating the corresponding mono-, bis-, tris- or tetrakis(bromoalkyl)porphycene.

Additional porphycene compounds are available by displacing the bromine atom or better the methanesulfonate group, which is prepared in high yield from the hydroxy compound, in $R^1$ groups having the formula $-(CH_2)_n-Br$ or $-(CH_2)_n-OSO_2CH_3$ respectively. For example, nucleophilic displacement of a bromide ion by cyanide, chloride, iodide, ammonia, primary amines ($NH_2R^2$), secondary amines ($HNR_2^2$), $H_2S$ and thiolate ions ($-SR^2$) provides porphycene compounds where $R^1$ is $-(CH_2)_n-X$ and X is I, Cl, CN, $NH_2$, $NHR^2$, $NR_2^2$, SH and $SR^2$. Conventional oxidation of the $SR^2$ group with known oxidizing agents yields the $S(O)_{1-2}R^2$ groups (Oae, in Oae, "The Chemistry of Sulfur", Plenum, New York, 1977). These aliphatic nucleophilic substitution reactions are well known in the art of organic synthesis (March, "Advanced Organic Chemistry, Reactions, Mechanisms, and Structure" 3rd Ed John Wiley & Sows, New York, 1985 and references cited therein).

Hydrolysis of the cyano porphycene compounds ($R^1$ is $-(CH_2)_n-CN$) with alcoholic hydrogen chloride provides the corresponding carboxylic esters in which $R^1$ is $-(CH_2)_n-COOR^2$. These are readily converted to the corresponding carboxylic acids, which can also be prepared by conventional hydrolysis methods but in low yield. Hydrolysis of the porphycene ester with alkali or alkaline earth metal hydroxide solutions yields the corresponding alkali and alkaline earth metal carboxylate salts by well known conventional hydrolysis reactions for example.

Carboxylic acid-containing porphycene compounds can further be converted to the acid halide by the conventional addition of thionyl bromide, chloride, $PBr_3$ or $PCl_3$. The acid halide derivative is then readily converted to the corresponding amide by the addition of ammonia, a primary amine or secondary amine to provide porphycene derivatives in which $R^1$ is —$(CH_2)_n$—$C(O)NH_2$, —$(CH_2)_n$—$C(O)NHR^2$, and —$(CH_2)_n$—$C(O)NR_2^2$. The acid halide derivative may also be converted to the corresponding ester ($R^1$ is —$(CH_2)_n$—$CO_2R^2$) by reaction with an alcohol ($HOR^2$). Esters may also be prepared by esterification of the carboxylic acid porphycene compounds using known esterification reactions. Porphycene derivatives in which $R^1$ is —$(CH_2)_n$—CHO can be readily prepared by reducing the carboxylic acid to the aldehyde using known reagents such as $(iso-Bu)_2AlH$ or by oxidizing the alcohol ($R^1$ is —$(CH_2)_{n-1}$—$CH_2OH$) using a weak oxidizing agent such as the chromium trioxide/pyridine, $MnO_2$ or other suitable reagents (see March, loc. cit.).

To improve water solubility of the porphycene compounds, a saccharide may be covalently attached to the porphycene via an ether linkage to provide porphycene compounds in which $R^1$ is —$(CH_2)_n$—O—G, where G is a monosaccharide. Preferred monosaccharides are pentose and hexose monosaccharides such as glucose, galactose, mannose, xylose, fructose, etc. The monosaccharide derivatives can be prepared by known chemistry, for example by reacting a porphycene containing at least one $R^1$ group having the formula —$(CH_2)_n$—OH with a OH-protected bromosaccharide, e.g., tetraacetyl bromoglucose. See the examples below and Fulling et al, Angew. Chem., 1989, 101:1550.

The monosaccharide-containing porphycene glycosides confer an increased level of hydrophilicity to the porphycene compounds which facilitates the preparation of aqueous solutions for pharmaceutical use. The glycosides have adequate solubility for preparation of aqueous, aqueous-alcoholic (preferably ethanolic) and aqueous dimethylsulfoxide (DMSO) solutions which may be directly topically applied for PDT therapy. Topical application of these aqueous solutions is particularly effective for treating psoriatic lesions. To increase water solubility the porphycene compounds may also be covalently attached to an amino acid or peptide by reaction of the substituent side chain, —$(CH_2)_n$—X (X=OH or halogen, for example) or —$(CH_2)_n$—CH=$CH_2$ with an alcohol/phenol-, a carboxyl-, an amine or a thiol-group of the amino acid or peptide.

The present invention includes porphycene metal complexes, for example zinc, nickel, magnesium and tin complexes, of the porphycene compounds described above. The invention also includes pharmaceutically acceptable acid and base addition salts of the porphycene compounds which may be prepared by the known addition of acids such as HCl, HBr, $H_2SO_4$, $H_3PO_4$, malic acid, tartaric acid, maleic acid, fumaric acid, etc. Base addition salts are prepared by the addition of alkali and alkaline earth metal salts such as sodium, potassium, calcium and magnesium carbonates, bicarbonates, sulfates, phosphates, etc. as well as by addition of ammonia, amines, preferably primary, secondary and tertiary $C_{1-6}$ alkyl amines, amino acids, etc. Any conventional acid or base addition salt which is pharmaceutically acceptable is considered to be within the scope of the present invention.

The porphycene compounds may also be covalently bonded to a stationary phase, such as beads, plates, fibers, etc. by reaction of the substituent side chain, —$(CH_2)_n$—X (X=OH or halogen, for example) or —$(CH_2)_m$—CH=$CH_2$ with a reactive group in the stationary support by addition or displacement reactions. When attached to a stationary solid phase, the porphycene compounds may be used to purify and decontaminate fluids passed over the solid phase. For example, blood for use in transfusions or from a patient undergoing plasmaphoresis procedures can be passed through a column containing resin beads having bound thereto the porphycene compounds of the present invention. Irradiation of the porphycene dye bound to the solid support at the absorption maximum wavelength for the particular porphycene dye results in the generation of singlet oxygen species which are lethal to viral, retroviral and bacterial contaminants in the blood or biological fluid. Addition of small amounts of the porphycene compounds into blood, followed by irradiation and subsequent transfusion into the patient undergoing therapy is also possible. The porphycene dyes are metabolized in vivo and excreted from the patient.

The porphycene compounds of the present invention may be formulated as therapeutic formulations for administration to patients in need of photodynamic therapy.

THERAPEUTIC FORMULATIONS

Therapeutic compositions containing the compounds of the present invention include liposome or microvesicle preparations, dispersions, solutions for parenteral injection, etc. and including topical dermatological preparations.

Parenteral Solutions

The photoactivatable porphycene dyes generally are used with additional solvents and adjuvants to prepare solutions suitable for intravenous injection. A number of solvents and co-solvents that are miscible with water and suitable surfactants can be used to achieve solutions for parenteral use. The most important solvents in this group are ethanol, polyethylene glycols of the liquid series and propylene glycol. A more comprehensive listing includes acetone, dimethyl acetamide, dimethyl formamide, dimethyl sulfoxide ethanol, glycerin, polyethylene glycol 300, and 400, propylene glycol, sorbitol, polyoxyethylene sorbitan fatty acid esters such as laureate, palmitate, stearate, and oleate, polyoxyethylated vegetable oil, sorbitan monopalmitate, 2-pyrrolidone; n-methyl-2-pyrrolidine; n-ethyl-1-pyrrolidine; tetrahydrofurfuryl alcohol, tween 80 and dimethyl isosorbide. Dimethyl isosorbide (ARLASOLVE ® DMI, ICI Specialty Chemicals) has the advantage of being both water- and oil-soluble. Additionally, dimethyl isosorbide may be readily gelled with a gelling agent to produce gel formulations with, for example, 4% KLUCEL ® (Hercules).

Other additives may be necessary to enhance or maintain chemical stability and physiological suitability-Examples are antioxidants, chelating agents, inert gases, buffers and isotonicifiers.

Examples of antioxidants and typical concentration ranges include acetone sodium bisulfite (0.1–0.8%), ascorbic acid (0.05–1.0%), monothioglycerol (0.1–1.0%), potassium metabisulfite (0.05–0.1%), propyl gallate (0.02%), sodium bisulfite (0.01–1.0%), sodium formaldehyde sulfoxylate (0.03–0.1%), sodium metabisulfite (0.02–0.25%), sodium sulfite (0.01–0.1%), sodium thioglycolate (0.05–0.1%).

Examples of chelating/complexing agents and typical concentration ranges include edetate sodium (0.005–0.1%), edetate calcium disodium (0.005%–0.01%), gentisic acid ethanolamide (1.0%–2.0%), niacinamide (1.0%–2.5%), sodium citrate (0.01%–2.5%), citric acid (0.001%–1.0%).

Examples of inert gases are nitrogen and carbon dioxide.

Buffers are used primarily to stabilize a solution against the chemical degradation that might occur if the pH changed appreciably. Buffer systems employed normally have as low a buffer capacity as feasible in order to not disturb significantly the body buffer systems when injected. The buffer range and effect of the buffer on activity must be evaluated. Appropriate adjustment is useful to provide the optimum conditions for pH dependent partition into the target malignant tissues or lesion area.

Examples of such buffer systems include the following acids: acetic, adipic, ascorbic, benzoic, citric, glycine, lactic, tartaric, hydrochloric, phosphoric, sulfuric, carbonic and bicarbonic; and their corresponding salts such as: potassium, sodium, magnesium, calcium and diethanolamine salts.

Osmoticity is of great importance and hypotonic solutions usually have their tonicity adjusted by the addition of salts such as sodium chloride, potassium chloride, magnesium chloride and calcium chloride and sugars such as dextrose, lactose, mannitol and sorbitol.

When the solution will be dispensed from multiple dose containers, antimicrobial agents in bacteriostatic or fungistatic concentrations must be added. Among the compounds and concentrations most frequently employed are phenylmercuric acid (0.002–0.01%), thimerosal (0.01%), benzethonium chloride (0.01%), benzalkonium chloride (0.01%), phenol or cresol (0.5%), chlorbutanol (0.5%), benzyl alcohol (2.0%), methyl p-hydroxybenzoate (0.18%), and propyl p-hydroxybenzoate (0.02%).

After the solution of the porphycene with its solvents and additives has been compounded, the solution is generally filtered to remove particulate matter above 2 μm in size and a further step eliminating particulate matter down to 0.2 μm can eliminate microorganisms and accomplish cold sterilization. The solution is filled under aseptic conditions. The final solution can be additionally sterilized in its final container by thermal methods such as autoclaving or non-thermal methods such as ionizing radiation. The process of freeze drying (lyophilization) can be employed to avoid adverse thermal and oxidative decomposition and provide enhanced stability and improved solubility.

The following formula provides an example of the utilization of various solvents and additives such as have been heretofore mentioned in the creation of a suitable parenteral solution of the porphycene. The formula is by way of example only and is not limiting to this invention. Suitable combinations and variations are obvious to those skilled in the art.

| Formula example for tetrakis(methoxyethyl)porphycene (TMEP) | |
| --- | --- |
|  | Grams |
| TMEP | 0.1 |
| Tetrahydrofurfurylalcohol | 40.0 |
| Polysorbate 20 | 1.0 |
| Sodium chloride | 0.9 |
| Citric acid buffer | 0.1 |
| water* enough to make 100 ml | |

*water may be water for injection, bacteriostatic water for injection or sterile water for injection.

Method of Preparation

1. Dissolve porphycene in tetrahydrofurfuryl alcohol and polysorbate 20, using heat and stirring as needed.
2. Dissolve sodium chloride and citrate buffer in water.*

*water may be water for injection, bacteriostatic water for injection or sterile water for injection.

3. Add the water solution slowly with stirring and heat as necessary to the solution.
4. Sterile fill using aseptic conditions and use terminal sterilization as needed.

This solution is suitable for a broad dosage range such as 0.1–10 mg/kg and preferably 0.2–5.0 mg/kg and may be infused as such or added to suitable large volume parenteral solutions such as dextrose, saline, ringers solutions for slower intravenous administration. Suitable solutions are described, for example, in REMINGTON'S PHARMACEUTICAL SCIENCES, 15th Ed., Easton: Mack Publishing Co. incorporated herein by reference.

Topical Formulations

The porphycene compounds of the present invention may be formulated for topical application in penetrating solvents or in the form of a lotion, cream, ointment or gel containing a sufficient amount of the porphycene compound to be effective for PDT therapy.

Suitable penetrating solvents are solvents for the porphycene compound which will enhance percutaneous penetration of the porphycene compound. Solvents which have this property include dimethyl sulfoxide, dimethyl acetamide, dimethylformamide, 1-methyl-2-pyrrolidone, diisopropyladipate, diethyltoluamide and to a lesser extent propylene glycol. Additional solvents include substituted azacycloalkan-2-ones having from 5 to 7 carbons in the cycloalkyl group such as 1-dodecylazacycloheptan-2-one (AZONE) and other azacycloalkan-2-ones such as described in U.S. Pat. No. 3,989,816 incorporated herein by reference.

Also included are N-bis-azocyclopentan-2-onyl alkanes described in U.S. Pat. No. 3,989,815 (hereby incorporated by reference), 1-substituted azacyclopentan-2-ones described in U.S. Pat. No. 3,991,203 (hereby incorporated by reference) and water-soluble tertiary amine oxides described in U.S. Pat. No. 4,411,893 (hereby incorporated by reference).

The topical formulations contain a sufficient amount of the porphycene compound to be effective in PDT therapy. Generally, concentrations in the range of 0.001 to 5 wt. %, preferably from about 1 to 5 wt. %, may be used. Typical lotion and cream formulations are shown below.

| \multicolumn{2}{c}{LOTION} |  |
| --- | --- |
| Parts by Weight | Ingredient |
| 5 | polyoxylene-40-sterate |
| 3 | sorbitan monostearate |
| 12 | *mixture of lanolin, mineral oil and lanolin alcohol |
| 6 | cetyl alcohol |
| 20 | soybean oil |
| 53.7 | water |
| 0.2 | methyl paraben |
| 0.1 | propyl paraben |

*AMERCOL BL (Amerchol Corp. Edison, N.J.)

| \multicolumn{2}{c}{CREAM} |  |
| --- | --- |
| Parts by Weight | Ingredient |
| 3 | polyoxylene-40-sterate |
| 2.5 | sorbitan monostearate |
| 10 | *mixture of lanolin, mineral oil and lanolin alcohol |
| 10 | cetyl alcohol |
| 1 | soybean oil |
| 73.2 | water |
| 0.2 | methyl paraben |
| 0.1 | propyl paraben |

*AMERCOL BL (Amerchol Corp. Edison, N.J.)

Additional topical formulations which may be used in conjunction with the porphycene compounds of the present invention are disclosed in U.S. Pat. No. 3,592,930 and U.S. Pat. No. 4,017,615 (hereby incorporated by reference).

Topical formulations may be prepared in gel form by combining the porphycene with a solvent such as diethyltoluamide (DEET) or diisopropyl adipate (DIPA) and adding a gelling agent. A preferred gelling agent is fumed silica (CAB-O-SIL®, Cabot Corp., Tuscola, Ill.), and particularly grade M-5. The gelling agent is generally used in amounts of about 5–12 wt % to obtain a gel with the desired viscosity. Obviously, gels containing more or less gelling agent will have slightly higher or lower viscosity. One skilled in the art can readily obtain the desired gel viscosity by adjusting the concentration of gelling agent. Additives, such as cosolvents and/or surfactants, frequently improve the gel properties and may be added as desired. Suitable cosolvents/surfactants include propylene glycol and glycerine. The additives may be incorporated into the gel by mechanically mixing the additives into a mixture of solvent and gelling agent.

Liposome or Microvesicle Preparations

Liposomes and methods of preparing liposomes are known and are described for example in U.S. Pat. No. 4,452,747 and U.S. Pat. No. 4,448,765 incorporated herein by reference. Liposomes are microvesicles which encapsulate a liquid within lipid or polymeric membranes. The porphycene compounds of the present invention may be incorporated into liposome microvesicles and used in this form for both topical and parenteral application. Topical and parenteral liposome preparations are known in the art. Sonified unilamellar liposomes made from certain unsaturated lipids are known stable carriers for some of the porphycenes of the invention.

U.S. Pat. No. 4,837,028 discloses injectable liposome formulations having enhanced circulation time. The liposomes have a size of about 0.08–0.5 microns, contain at least 50 mole % of a membrane rigidifying component such as sphingomyelin and further contain about 5–15 mole % ganglioside $G_{M1}$. Liposome preparations for encapsulating sparingly soluble pharmaceutical compounds are disclosed in U.S. Pat. No. 4,721,612. The specification of these U.S. patents is incorporated herein by reference.

After administration of a therapeutically effective amount of one or more of the porphycene compounds in the pharmaceutical composition or preparation, to a patient having a treatable condition such as a solid tumor (cancer) or psoriasis, for example, the patients affected body area is exposed to a therapeutically sufficient amount of light having an appropriate wavelength for absorption by the particular porphycene compound used. Suitable wavelengths are generally from about 600 to about 900 nm, preferably from about 600 to about 650 nm, more preferably 620–650 nm. Irradiation of the accumulated porphycene generates singlet oxygen which is thought to be the actual lethal species responsible for destruction of the neoplastic cells.

Photodynamic therapy using the porphycene compounds of the present invention has a number of advantages. The porphycene compound itself is minimally toxic in the unexcited state. Each porphycene molecule can be repeatedly photoactivated and lead each time to cell-lethal events, that is, the generation of singlet molecular oxygen. The half-life of singlet molecular oxygen is approximately four microseconds in water at room temperature. The target cell is therefore affected without the opportunity for migration of the lethal singlet molecular oxygen to neighboring healthy tissue cells. Preferably, the singlet oxygen molecules rupture chemical bonds in the target cell wall or mitochondria resulting in destruction of the target cell. Destruction of target cell tissue commences promptly upon irradiation of the porphycene compounds. Indirect target cell death can also result from destruction of the tumor vascular system with concomitant restriction of oxygen supply.

Photodynamic therapy using the compounds of the present invention is therefore selective and minimally toxic to healthy tissue. Singlet oxygen molecules produced which do not react rapidly decay to harmless ground state oxygen molecules.

A variety of phototherapy and irradiation methodologies are known to those skilled in the art and can be used with the novel porphycene compounds of the present invention. The time and duration of therapy and repetition of the irradiation treatment can be selected by the therapist (physician or radiologist) according to known photodynamic therapy criteria. The dosage of the porphycene compound may be varied according to the size and location of the target tissues which are to be destroyed and the method of administration. Generally, the dosage will be in the range of 0.05–10 mg of porphycene compound per kilogram of body weight, more preferably in the range of 0.1–5.0 mg/kg.

Irradiation generally takes place not less than one hour nor more than four days after parenteral administration of the porphycene compound. Usually, phototherapy is begun approximately 3 hours to 48 hours after administration of the photodynamic therapy agent. With topically administered dye, radiation may commence as soon as 10 minutes after dye application for treatment of psoriasis, genital warts, bacterial infections, etc. Exposure to non-therapeutic light sources should be avoided immediately following phototherapy to minimize light toxicity. Appropriate draping of the patient can be used to limit the area affected by phototherapy.

Light sources which are appropriate for use are well known in the art and may vary from white light sources with appropriate filters to lasers. As noted above, preferred wavelengths are from 600 to 950 nm, preferably from about 600 to about 800 nm. The total amount of light which is applied to the affected area will vary with the method used and the location of the tumor or topical lesion. Generally, the amount of light is in the range of about 50 to 1000 J-cm$^2$ preferably in the range of 100 to 350 J-cm$^2$.

Having generally described this invention, a further understanding can be obtained by reference to certain specific examples which are provided herein for purposes of illustration only and are not intended to be limiting unless otherwise specified. Procedures which are constructively reduced to practice herein are described in the present tense and procedures which have been carried out in the laboratory are set forth in the past tense.

EXAMPLES

Zinc/copper Pair

A solution of 20 g (0.1 mol) Cu(OAc)$_2$—H$_2$O in 400 mL of glacial acetic acid was treated rapidly with 196 g (3 mol) zinc powder with vigorous stirring. Within 15 seconds the solution discolored and was subsequently stirred for 30 seconds. The solution was then filtered under inert gas and washed in succession twice with acetone, toluene, and absolute THF. The Zn/Cu pair thus produced can be used without drying.

5-Methoxy-3-oxopentanic acid alkylester (1) (see FIG. 1)

68 g (0.8 mol) of 3-methoxypropionitrile were dissolved in 1000 mL THF freshly distilled over LiAlH$_4$ and treated with 150.3 g (2.2 mol) Zn/Cu pair under inert gas. With moderate reflux 267.2 g (1.6 mol) of 2-bromoacetic acid ethyl ester were added drop-by-drop to the vigorously stirred suspension within 75 minutes. After the reaction had started, the heat was turned off and the slight reflux adjusted via the drop velocity. To complete the reaction, the solution was stirred for 30 minutes at the boiling temperature of THF. Then, 420 mL of 10% HCl were added drop-by-drop within 30 minutes at 15° C. and stirred for another 30 minutes. The solution was filtered from the non-converted zinc and the filtrate was extracted three times with 300 mL of CHCl$_3$ each. The organic phases were washed four times with water and once with 5% NaHCO$_3$ solution and the solvent was removed following drying over MgSO$_4$ under vacuum. The obtained reddish liquid was distilled under oil pump vacuum. The fraction at 85° C./0.5 torr yielded 106.8 g (0.62 mol) of 5-methoxy-3-oxopentanic acid ethyl ester as a colorless, fruity smelling oil with a refractive index n$_D^{22}$=1.434. The yield was to 77.5% based on 3-methoxypropionitrile.

Elementary analysis: calculated: C 55.16% H 8.10% found: C 54.82% H 7.92%

If 2-bromoacetic acid methyl ester is added as the α-bromoester, 97.2 g (0.61 mol) of 5-methoxy-3-oxopentanic acid methyl ester having a boiling point of 62°-63° C./0.12 torr are obtained with the same method. The refractive index of the colorless oil, which was produced in a yield of 76% based on 3-methylpropionitrile, is n$_D^{21}$=1.435.

$^1$H-NMR spectrum of (1a) (CDCl$_3$, 80 MHz), δ (ppm)=2.62 (triplet, 2H) MeOCH$_2$CH$_2$; 3.16 (singlet, 3H) CH$_3$OCH$_2$; 3.35 (singlet, 2H) COCH$_2$CO; 3.48 (triplet, 2H) MeOCH$_2$; 3.56 (singlet, 3H) CO$_2$CH$_3$; signals at 4.9 (singlet) and 2.3 ppm (triplet) through the enol form present in the equilibrium.

Mass spectrum of (1a), EI, 70 eV: m/z=160 (M+, 3%); 129 (M—OMe+, 12%); 101 (M—CO$_2$Me+, 40%); 100 (M—MeOCH$_2$—CH$_3$+, 33%); 87 (M—CH$_2$CO$_2$Me+, 85%).

$^1$H-NMR spectrum of (1b), CDCl$_3$, 80 MHz, δ (ppm)=1.06 (triplet, 3H) CH$_2$CH$_3$; 2.57 (triplet, 2H) MeOCH$_2$CH$_2$; 3.10 (singlet, 3H) CH$_3$OCH$_2$; 3.28 (singlet, 2H) COCH$_2$CO; 3.43 (triplet, 2H) MeOCH$_2$; 3.97 (quartet, 2H) CH$_2$CH$_3$.

Mass spectrum of (1b), EI, 70 eV: m/z=174 (M+, 1%); 143 (M—OMe+, 12%); 100 (M—MeOCH$_2$—CH$_2$CH$_3$+, 40%); 87 (M—CH$_2$CO$_2$Et+, 85%).

IR spectrum of (1b), film: ν (cm$^{-1}$)=2987, 2941, 2903 (CH), 1743, 1724 (C=O), 1118 (C—O, ether)

2.4-Bis(alkoxycarbonyl)-3-methoxyethyl-5-methylpyrroles (2)

While stirring and ice cooling, a cold saturated aqueous solution of 42 g (0.6 mol) sodium nitrite was added so slowly drop-by-drop to a solution of 104.4 g (0.6 mol) methoxypentanoic acid ethyl ester in 450 mL of glacial acetic acid, that no noticeable NO$_x$ development was detected. The solution was stirred for two hours and treated with 83.2 g (0.64 mol) acetoacetic acid ethyl ester. Then while stirring vigorously, a mixture of 80 g (1.22 mol) of zinc powder and 100 g (1.22 mol) sodium acetate was added in portions within 40 minutes. The inner temperature ranged from 80° to 85° C., a state that was reached by cooling occasionally. Following completion of the addition, the solution was stirred another 30 minutes and then filtered from the nonreacted zinc. The warm solution was poured into 4 L of water and left standing overnight to complete the precipitation. The raw product was filtered off, washed with a little ice cold ether, dried over P$_4$O$_{10}$ under vacuum for one day, and recrystallized from ethanol/water. Thus, 113.2 g (0.4 mol) 2,4-bis(ethoxycarbonyl)-3-methoxyethyl-5-methylpyrrole (2b) was obtained as colorless needles with a melting point of 86° C. Yield: 65% based on (1b). For further reaction of (2b) it was not necessary to recrystallize the raw product from ethanol/water.

Elementary analysis: calculated: C 59.16% H 7.47% N 4.94% found: C 59.24% H 7.33% N 4.99%

The workup to isolate the corresponding pyrrol-dimethyl ester (2a) was the same as in the case of the application of 96 g (0.6 mol) 5-methoxy-3-oxopentanoic acid methyl ester (1a) and 74.2 g (0.64 mol) acetoacetic acid methyl ester. However, the mother liquor of the first crystallization was extracted once with CHCl$_3$ and the solid obtained following neutralization and drying over MgSO$_4$ and evaporation of the solvent was combined with the quantity of substance that precipitated first. In this case recrystallization from methanol/water for esterification was avoided. The result was 96.4 g (0.38 mol) colorless needles of 2,4-bis (methoxycarbonyl) 3-methoxyethyl-5-methylpyrrole (2a), which melt at 118° C. Yield: 63%.

Elementary analysis: calculated: C: 56.46 H: 6.71 N: 5.49 found: C: 56.42 H: 6.96 N: 5.45

$^1$H-NMR spectrum of (2a), CDCl$_3$, 300 MHz, δ (ppm)=2.45 (singlet, 3H) α—CH$_3$; 3.33 (singlet, 3H) CH$_3$OCH$_2$; 3.33 (triplet, 2H) MeOCH$_2$CH$_2$; 3.50 (triplet, 2H) MeOCH$_2$; 3.77 (singlet, 3H) β—CO$_2$CH$_3$; 3.80 (singlet, 3H) α—CO$_2$CH$_3$; 9.98 (wide singlet) NH.

$^{13}$C-NMR spectrum of (2a), CDCl$_3$, 75.5 MHz, δ (ppm)=14.01 (α—CH$_3$); 25.57 (MeOCH$_2$CH$_2$); 50.66 (β—CO$_2$CH$_3$); 51.36 (α—CO$_2$CH$_3$); 58.1 H$_3$COCH$_2$); 72.78 (MeOCH$_2$CH$_2$); 112.88 (C-4); 118.21 (C-2); 130.80 (C-3); 139.86 (C-5) 161.94 (β—CO$_2$CH$_3$); 165.44 (α—CO$_2$CH$_3$).

Mass spectrum of (2a), EI, 70 eV: m/z=255 (M+, 12%); 223 (M—MeOH+, 77%); 201 (M—MeOCH$_2$+, 47%); 178 (M—MeOH—MeOCH$_2$+, 100%).

IR spectrum of (2a), KBr pellet: ν (cm$^{-1}$)=3306, (NH); 2962, 2943, 2868 (CH), 1711 (C=O).

UV/VIS spectrum of (2a) CH$_2$Cl$_2$, λmax[nm] (ε)=227 (1.4×10$^4$); 270 (1.6×10$^4$).

$^1$H-NMR spectrum of (2b), CDCl$_3$, 80 MHz, δ (ppm)=1.33 (2 triplets, 6H) CH$_2$CH$_3$; 2.48 (singlet, 3H) α—CH$_3$; 3.35 (singlet, 3H) CH$_3$OCH$_2$; 3.45 (A$_2$B$_2$ system, 4H) MeOCH$_2$CH$_2$; 4.27 (quartet, 2H) β—CO$_2$CH$_2$CH$_3$; 4.32 (quartet, 2H) α—CO$_2$CH$_2$CH$_3$; 9.5 (wide singlet): NH.

IR spectrum of (2b) KBr pellet: ν (cm$^{-1}$) 3289, (NH); 2989, 2932, 2891 (CH); 1703, 1663 (C=O); 1438 (CH).

Mass spectrum of (2b) EI, 70 eV: m/z=283 (M+, 13%); 251 (M—MeOCH$_2$+, 15%); 164 (M—MeOCH$_2$—CH$_3$—EtOH+, 18%).

UV/VIS spectrum of (2b), CH$_2$Cl$_2$, λmax[nm] (ε)=226 (1.3×10$^4$); 271 (1.6×10$^4$).

3,5-Bis(alkoxycarbonyl)-2-carboxy-4-methoxyethylpyrroles (3)

At one time 48 g (0.3 mol) of distilled bromine were added to a solution of 85 g (0.3 mol) α-methylpyrroldiethyl ester in 280 mL glacial acetic acid and 55 mL of acetic anhydride at 0° C. Subsequently 128.5 g (1.05 mol) freshly distilled sulfuryl chloride were added drop-by-drop at this temperature in the dark over a period of two hours. Since the reaction solution becomes viscous in the interim, the use of a KPG ® stirrer is recommended. The red solution obtained was then stirred at 0° C. for two hours. Then, 190 mL of water were added dropwise within 30 minutes, and the inner temperature rose to 70° C. After another 30 minutes of stirring, the mixture precipitated out by pouring in 2.5 L of water. It was left standing overnight and was filtered the next day. If the result was an oily raw product, it was decanted. At this stage the mixture was suspended in 2 L of 70° C. warm water and treated in portions with solid NaHCO$_3$ until the generation of gas was no longer observed. It was filtered and slowly neutralized with semiconcentrated HCl while stirring vigorously. The mixture was left standing at 0° C. for eight hours in order to complete the precipitation and the resulting fine crystalline solid was filtered off. The pyrrolcarboxylic acid (3b) was recrystallized from ethanol/water and dried under vacuum for two days. 47 g (0.15 mol) of colorless needles having a solid point of 136° C. were obtained. The yield of (3b) was 50%. For further reaction of (2b) it was not necessary to recrystallize the raw product from ethanol/water.

With the same method, 76.5 g (0.3 mol) methylpyrroldimethyl ester (2a) yield, following recrystallization from MeOH/water, 42.8 g (0.15 mol) of 3,5-bis(methoxycarbonyl)-2-carboxy-4-methoxyethylpyrrole (3a). The colorless needles have a melting point of 142° C. The yield was 50%.

$^1$H-NMR spectrum of (3a), CDCl$_3$, 300 MHz, δ (ppm)=3.36 (singlet, 3H) CH$_3$OCH$_2$; 3.45 (A$_2$B$_2$ system, 4H) MeOCH$_2$CH$_2$; 3.91 (singlet, 3H) β—CO$_2$CH$_2$CH$_3$; 4.02 (singlet, 3H) α—CO$_2$CH$_3$; 10.30 (wide singlet) NH.

IR spectrum of (3a), KBr pellet: ν (cm$^{-1}$) 3247 (NH); 2958, 2900 (CH), 2616 (OH); 1722, 1632 (C=O); 1441 (CH).

Mass spectrum of (3a), EI, 70 eV: m/z=285 (M+, 28%); 270 (M—CH$_3$+, 11%); 253 (M—MeOH+, 85%); 222 (M—MeOH—MeO+, 100 %); 208 (M—MeOCH$_2$—MeOH+, 75%).

1H-NMR spectrum of (3b), CDCl$_3$, 80 MHz, δ (ppm)=1.38 (triplet, 3H) β—CO$_2$CH$_2$CH$_3$; 1.45 (triplet, 3H) α—CO$_2$CH$_2$CH$_3$; 3.33 (singlet, 3H) CH$_3$OCH$_2$; 3.46 (A$_2$B$_2$ system, 4H) MeOCH$_2$CH$_2$; 4.40 (quartet, 2H) β—CO$_2$CH$_2$CH$_3$; 4.50 (quartet, 2H) α—CO$_2$CH$_2$CH$_3$; 10.25 (wide singlet) NH; 14.64 (wide singlet) CO$_2$H.

IR spectrum of (3b), KBr pellet: ν (cm$^{-1}$) 3258, (NH); 2980, 2934, 2881 (CH), 2568 (OH); 1737, 1693 (C=O); 1116 (C-0, ether).

Mass spectrum of (3b), EI, 70 eV: m/z=313 (M+, 34%); 281 (M—MeOH+, 41%); 252 ([M—EtOH—CH$_3$+, 28%); 222 (M—MeOCH$_2$—EtOH+, 48%).

UV/VIS spectrum of (3b), CH$_2$Cl$_2$, λmax[nm] (ε)=237 (2.7×10$^4$); 257 (9.2×10$^3$); 288 (8.0×10$^3$).

3,5-Bis(alkoxycarbonyl)-2-iodo-4-methoxyethylpyrroles (4)

While stirring, 47 g (0.15 mol) bis(ethoxycarbonyl) pyrrole carboxylic acid were suspended in 350 mL of water and treated in portions with 40.9 g (0.48 mol) of sodium hydrogen carbonate at 75° C. At this stage a solution of 38.1 g (0.15 mol) I$_2$ and 49.8 g (0.3 mol) KI in 280 Ml of water were added dropwise to this clear solution within two hours. The reaction solution foamed due to the resulting CO$_2$. The product (4b) began to precipitate after some time. Following completion of the addition, the temperature was maintained for another 30 minutes while stirring and then the still warm reaction solution was poured on 700 g of ice. The precipitate was filtered off, washed with water and ice cold pentane and recrystallized from ethanol so that colorless needles were obtained. The 53.3 g (0.135 mol) of the title compound that were obtained following drying under vacuum exhibit a melting point of 132° C. Yield: 90%.

Elementary analysis: calculated: C 39.51% H 4.59% N 3.54% found: C 39.36% H 4.54% N 3.45%

When 42.8 g (0.15 mol) bis(methoxycarbonyl) pyrrolcarboxylic acid (3a) were used, 49.5 g (0.135 mol) iodopyrroledimethyl ester (4a) in 90% yield was obtained following recrystallization from methanol with the same procedure. The melting point of the colorless needles was 114° C.

1H-NMR spectrum of (4a), CDCl$_3$, 80 MHz, δ (ppm)=3.35 (singlet, 3H) H$_3$COCH$_2$; 3.45 (A$_2$B$_2$ system, 4H) MeOCH$_2$CH$_2$; 3.84 (singlet, 3H) β-CO$_2$CH$_3$; 3.88 (singlet, 3H) α—CO$_2$CH$_3$; 9.54 (wide singlet) NH.

Mass spectrum of (4a), EI, 70 eV: m/z=367 (M+, 28%); 355 (M—MeOH+, 100%); 322 (M—MeOCH$_2$+, 35%); 290 (M—MeOCH$_2$—MeOH+, 59%).

IR spectrum of (4a), KBr pellet: $\nu$ (cm$^{-1}$)=3263 (NH); 2955, 2902 (CH), 1676 (C=O); 1440 (CH); 1120 (C-0, ether).

UV/VIS spectrum of (4a) MeOH, CH$_2$Cl$_2$, $\lambda$max[nm] ($\epsilon$)=222 (2.0×10$^4$); 266 (1.8×10$^4$). 1H-NMR spectrum of (4b), CDCl$_3$, 80 MHz, $\delta$ (ppm)=1.36 (triplet, 3H) $\beta$—CO$_2$CH$_2$C$\underline{H}_3$; 1.37 (triplet, 3H) $\alpha$—CO$_2$CH$_2$C$\underline{H}_3$; 3.34 (singlet, 3H) C$\underline{H}_3$OCH$_2$; 3.46 (A$_2$B$_2$ system, 4$\overline{H}$) MeOC$\underline{H}_2$C$\underline{H}_2$; 4.33 (quartet, 2H) $\beta$—CO$_2$C$\underline{H}_2$CH$_3$; 4.36 (quartet, 2H) $\alpha$—CO$_2$C$\underline{H}_2$CH$_3$; 9.5 (wide singlet) N$\underline{H}$.

Mass spectrum of (4b), EI, 70 eV: m/z=395 (M+, 30%); 363 (M—MeOH+, 100%); 322 (M—CO$_2$Et+, 31%); 276 (M—EtOH—CH$_2$H$_5$—MeOCH$_2$+, 42%).

IR spectrum of (4b), KBr pellet: $\nu$ (cm$^{-1}$) 3140 (NH); 2989, 2830 (CH), 1707 (C=O); 1105 (C-0, ether).

UV/VIS spectrum of (4b), CH$_2$Cl$_2$, $\lambda$max[nm] ($\epsilon$)=227 (1.4×10$^4$); 267 (1.8×10$^4$).

3,3',5,5'-Tetrakis(alkoxycarbonyl)-4,4'-bis(methoxyethyl) 2,2'-bipyrroles (5)

45 g (0.7 mol) copper bronze were added to a solution of 49.1 g (0.12 mol) of iodopyrrolediethyl ester in 250 mL of absolute dimethylformamide and the mixture was stirred at room temperature for twenty hours. In so doing, the suspension assumed a greenish-brown color. The raw product was subsequently precipitated by slowly adding 1.2 L of water and filtering off over Celite ® together with the non-converted copper. The filter residue was extracted with 400 mL of hot chloroform. The extract was washed briefly with 20% HNO$_3$, twice with water and once with 5% NaHCO$_3$ solution. After drying over MgSO$_4$ the solvent was evaporated and the remaining solid was digested with 50 mL of cold hexane and subsequently dried under oil pump vacuum. Following recrystallization from ethanol, 39.9 g (74.4 mmol) of bipyrroltetraethyl ester (5b) were obtained in the form of matted needles having a melting point of 150° C. Yield: 67%

Elementary analysis: calculated: C 58.20% H 6.76% N 5.22% found: C 58.05% H 6.72% N 5.25%

Under analogous condition, 45.5 g (94.8 mmol) of bipyrrole (5a) was recovered from 44 g (0.12 mol) of the iodopyrroledimethyl ester (4a) following recrystallization from methanol. The melting point of the colorless, matted needles was at 221° C. Yield: 79%.

$^1$H-NMR spectrum of (5a), CDCl$_3$, 80 MHz, $\delta$ (ppm)=3.38 (singlet, 6H) $\underline{H}_3$COCH$_2$; 3.50 (A$_2$B$_2$ system, 8H) MeOC$\underline{H}_2$C$\underline{H}_2$; 3.96 (singlet, 6H) $\beta$—CO$_2$C$\underline{H}_3$; 3.98 (singlet, 6H) $\alpha$—CO$_2$C$\underline{H}_3$; 13.95 (wide singlet) N$\underline{H}$.

Mass spectrum of (5a), FAB, 75 eV: m/z=480 (M+, 76%); 449 (M—MeO+, 40%); 417 (M—MeO—H—MeO+, 24%); 403 (M—MeOCH$_2$—MeOH+, 12%); 307 (M—4MeOH—MeOCH$_2$+, 33%).

IR spectrum, KBr pellet, $\nu$ (cm$^{-1}$)=2953, 2985 (CH), 1711 (C=O), 1451, 1311.

UV/VIS spectrum of (5a), CHCl$_3$, $\lambda$max[nm] ($\epsilon$)=250 (2.5×10$^4$); 288 (1.5×10$^4$); 346 (2.2×10$^4$).

IR spectrum of (34b), KBr pellet: $\nu$ (cm$^{-1}$)=2988, 2893 (CH), 1716 (C=O), 1479, 1383 (CH); 1117 (C-0, ether).

$^1$H-NMR spectrum of (5b), CDCl$_3$, 80 MHz, $\delta$ (ppm)=1.41 (triplet, 3H) $\beta$—CO$_2$CH$_2$C$\underline{H}_3$; 1.42 (triplet, 3H) $\alpha$—CO$_2$CH$_2$C$\underline{H}_3$; 3.34 (singlet, 6$\overline{H}$) $\underline{H}_3$COCH$_2$; 3.49 (A$_2$B$_2$ system, 8$\overline{H}$) MeOC$\underline{H}_2$C$\underline{H}_2$; 4.39 (quartet, 4H) $\beta$—CO$_2$C$\underline{H}_2$CH$_3$; 4.43 (quartet, 4H) $\alpha$—CO$_2$C$\underline{H}_2$CH$_3$; 14.10 (wide singlet) N$\underline{H}$.

Mass spectrum of (5b) EI, 75 eV: m/z=536 (M+, 100%); 504 (M—MeOH+, 3%); 490 (M—MeO—CH+, 11%); 445 (M—MeOCH$_2$—EtOH+, 26%).

UV/VIS spectrum of (5b), CH$_2$Cl$_2$, $\lambda$max[nm] ($\epsilon$)=228 (1.9×10$^4$); 249 (2.6×10$^4$); 289 (1.5×10$^4$); 347 (2.3×10$^4$).

3,3',5,5'-Tetracarboxy-4,4'-bis(methoxyethyl)-2,2'-bipyrrole (6)

A solution of 26.8 g (50 mmol) of bipyrrole tetraethyl ester (5b) or 24 g (50 mmol) of tetramethyl ester (5a) in 1350 mL of methanol were treated with a solution of 30 g (0.75 mol) NaOH in 540 mL of water and heated with reflux for 40 hours. Following distillation of methanol, the mixture was diluted with water to 4 L and slowly neutralized with diluted hydrochloric acid while stirring. The mixture was stirred at the neutral point for fifteen minutes at room temperature and then precipitated at pH 2 with the further addition of acid. The mixture was left standing at 0° C. for six hours and the precipitate was filtered, washed with water and dried for five days over P$_4$O$_{10}$ under vacuum. 1.5 g (46 mmol) of a colorless to slightly greenish powder was obtained in that, following recrystallization from DMSO/water yielded a microcrystalline, colorless substance, which decomposed at 248° C.

Elementary analysis: calculated: C 50.95% H 4.75% N 6.60% found: C 50.94% H 4.87% N 6.47%

$^1$H-NMR spectrum of (6), DMSO-d$_6$, 300 MHz, $\delta$ (ppm)=3.23 (singlet, 6H) $\underline{H}_3$COCH$_2$; 3.40 (A$_2$B$_2$ system, 8H) MeOC$\underline{H}_2$C$\underline{H}_2$; 12.70 (very wide singlet) CO$_2\underline{H}$; 13.15 (wide singlet) N$\underline{H}$.

$^{13}$C-NMR spectrum of (6), DMSO-d$_6$, 75.5 MHz, $\delta$ (ppm) =25.27 (MeO$\underline{C}$H$_2$CH$_2$); 57.61 (H$_3$CO$\underline{C}$H$_2$); 72.50 (MeO$\underline{C}$H$_2$CH$_2$); 114.83, 120.52, 129.61, 132.68 (C-2, 3, 4, 5); 161.78, 167.22 ($\underline{C}$O$_2$H).

UV/VIS spectrum of (6), DMSO, $\lambda$max[nm] ($\epsilon$)=258 (1.5×10$^4$); 277 (1.5×10$^4$); 343 (1.3×10$^4$).

Mass spectrum of (6), EI, 70 eV: m/z=292 (M—3-CO$_2$+, 10%); 248 (M—4CO$_2$+, 36%); 203 (M—4CO$_2$-MeOCH$_2$+, 26%); 171 (M—4CO$_2$—MeOCH$_2$—MeOH+, 100%).

IR spectrum of (6), KBr pellet, $\nu$ (cm$^{-1}$)=2922 (CH), 1633 (C=O), 1554, 1187, 756.

4,4'-Bis(methoxyethyl)-2,2'-bipyrrole (7)

8.5 g (20 mmol) of bipyrrole tetracarboxylic acid (6) were decarboxylated in a sublimator at 230° C. (bath temperature)/0.1-0.2 torr. The product (7) separated as a colorless, amorphous or pale green crystalline solid. The bipyrrole (7) decomposed slowly above 75° C. and melts when rapidly heated at 98° C. Weighing yielded 4.7 g (18.8 mmol) of the title compound in a 94% yield.

The bipyrrole was sensitive to acid and oxygen and was stored under protective gas at low temperature.

$^1$H-NMR spectrum of (7), acetone-d$_6$, 300 MHz, $\delta$ (ppm)=2.64 (triplet, 4H) MeOCH$_2$C$\underline{H}_2$; 3.27 (singlet, 6H) $\underline{H}_3$COCH$_2$; 3.46 (triplet, 4H) MeOC$\underline{H}_2$CH$_2$; 6.11 (multiplet, 2H) H at C-3; 6.2 (multiplet, 2$\overline{H}$) H at C-5; 9.79 (wide singlet) N$\underline{H}$.

Mass spectrum of (7), EI, 70 eV: m/z=248 (M+, 82%); 203 (M—MeOCH$_2$+, 28%); 171 (M—MeOCH$_2$—MeOH+, 100%); 157 (M—MeOCH$_2$—MeOCH$_3$+, 33%).

IR spectrum (7), KBr pellet, $\nu$ (cm$^{-1}$)=3284 (NH); 3123, 3089, 2949, 2852 (CH) 1568, 1185, 1082, 946, 802.

UV/VIS spectrum of (7), CH$_3$CN, λmax[nm] (ε)=343 (8.0×10$^2$); 284 (1.8×10$^4$).

5,5'-Diformyl-4,4'-bis(methoxyethyl)-2,2-bipyrrole (8)

6.14 g (40 mmol) of distilled phosphoryl chloride was added dropwise to a solution of 2.48 g (10 mmol) bipyrrole (7) in 50 mL of absolute dimethylformamide under protective gas at 0° C. within 30 minutes. The mixture was heated to 60° C. for one hour and subsequently poured into a solution of 60 g sodium acetate in 480 mL of water. The mixture was stirred for one hour at 85° C., wherein the dialdehyde (8) precipitated out in yellow flakes. The solution was cooled to 0° C., the precipitate filtered off and washed with cold water. After drying over P$_4$O$_{10}$ under vacuum, 2.58 g (8.5 mmol) of the title compound which was recrystallized from tetrahydrofuran, were obtained. The title compound decomposes at 186° C. without melting. The yield was 85%.

Elementary analysis: calculated: C: 63.14 H: 6.62 N: 9.21 found: C: 63.07 H: 6.54 N: 9.15

$^1$H-NMR spectrum of (8), CDCl$_3$, 300 MHz, δ (ppm)=3.03 (triplet, 4H) MeOCH$_2$C$\underline{H}_2$; 3.37 (singlet, 6H) $\underline{H}_3$COCH$_2$; 3.62 (triplet, 4H) MeOC$\underline{H}_2$CH$_2$; 6.54 (doublet, 2H) H at C-3; 9.7 (singlet, 2H) C$\underline{H}$O; 12.27 (wide singlet) N$\underline{H}$.

$^{13}$C-NMR spectrum of (8), 75.5 MHz, δ (ppm)=26.03 (MeOCH$_2$$\underline{C}$H$_2$); 58.74 ($\underline{H}_3$COCH$_2$); 72.91 (MeO$\underline{C}$H$_2$CH$_2$); 111.79, 130.60, 131.57, 136.10 (C-2, 3, 4, 5), $\overline{177.71}$ (C-5$^1$).

Mass spectrum of (8), EI, 75 eV: m/z=304 (M+, 100%); 272 (M—MeOH+, 9%); 227 (M—MeOCH$_2$—MeOH+, 19%); 199 (M—MeOCH$_2$—MeOH—CO+, 19%).

IR spectrum of (8), KBr pellet: ν (cm$^{-1}$)=3266 (NH); 2925, 2868 (CH), 1648 (C=O), 1116 (C-0, ether) 1607, 809.

UV/VIS spectrum of (8), CH$_2$Cl$_2$ λmax[nm] (ε)=235 (9.6×10$^3$); 271 (1.5×10$^4$); 381 (3.6×10$^4$).

2,7,12,17-Tetrakis(methoxyethyl)porphycene (9)

Under protective gas over 10 minutes, 16.5 ml (0.15 mol) TiCl$_4$ were added dropwise to a suspension of 19.6 g (0.3 mol) zinc powder and 1.95 g (9.5 mmol) CuCl in 800 mL of THF freshly distilled over LiAlH$_4$. Subsequently the mixture was heated with reflux for three hours. At this stage a solution of 1.83 g (6 mmol) dialdehyde (8) in 600 mL of absolute THF was added dropwise within 20 minutes to the black McMurry reagent thus prepared while stirring vigorously. The reaction can be followed by means of thin layer chromatography (silica gel/CH$_2$Cl$_2$). The reaction was stirred for ten minutes at the boiling temperature of the tetrahydrofuran and then cooled to 0° C. At this temperature 300 ml of 6% NH$_3$ solution were added dropwise over one hour. The reaction mixture was treated with 600 mL of dichloromethane and filtered off over Celite ® after fifteen minutes of stirring. The residue was extracted with another 200 mL of CH$_2$Cl$_2$ and the combined organic phases were washed three times with 300 mL of water. Following drying over MgSO$_4$, the solvent was evaporated under vacuum and the residue was chromatographed with CH$_2$Cl$_2$ on Al$_2$O$_3$ (Brockmann, II--III activity, column 5×10 cm). The first blue, red fluorescing fraction was collected and rechromatographed with CH$_2$Cl$_2$/ethylacetate/methanol (100:20:1) on silica gel (column 4×40 cm) in order to separate any possibly existing small quantities of degraded porphycenes as a small blue fraction, which was eluted prior to the title compound. Following evaporation of the solvent and crystallization from CH$_2$Cl$_2$/MeOH, (9) was obtained in the form of long, violet, metallically glistening needles having a melting point of 172° C. A 25% yield of 406 mg (0.75 mmol) of the porphycene tetraether (9) was obtained.

Elementary analysis: calculated C 70.83% H 7.06% N 10.32% found C 70.71% H 6.93% N 10.40%

$^1$H-NMR spectrum of (9), CDCl$_3$, 300 MHz, δ (ppm)=3.11 (wide singlet) N$\underline{H}$; 3.60 (singlet, 12H); 4.31 (singlet, 16H) MeOC$\underline{H}_2$C$\underline{H}_2$; 9.34 (singlet, 4H) H at C-3, 6, 13, 16; 9.71 (singlet, 4$\overline{H}$) H at C-9, 10, 19, 20.

$^{13}$C-NMR spectrum of (9), CDCl$_3$, 75.5 MHz, −60° C., δ (ppm)=8.57 (C-MeOCH$_2$CH$_2$; 59.24 (H$_3$COCH$_2$); 73.54 (MeO$\underline{C}$H$_2$CH$_2$); 110.41 ($\overline{C}$-9, 10, 19, 20); 123.37 (C-3, 6, 13, $\overline{16}$); 133.54 (C-4, 5, 4, 15); 140.28, 142.80 (C-1, 2, 7, 8, 11, 12, 17, 18).

Mass spectrum of (9) EI, 75 eV: m/z=542 (M+, 81%); 497 (M—MeOCH$_2$+, 100%); 452 (M—2-MeOCH$_2$+, 20%); 407 (M—3MeOCH$_2$+, 24%); 375 (M—3MeOCH$_2$—MeOH+, 3%).

IR spectrum; CsI pellet, ν (cm$^{-1}$) 2920, 2867 (CH), 1113 (C-0, ether) , 1459, 1017, 816.

UV/VIS spectrum of (9) CH$_2$Cl$_2$, λmax[nm] (ε)=370 (1.4×10$^5$); 563 (3.5×10$^4$); 602 (3.3×10$^4$); 634 (4.7×10$^4$).

$^1$H-NMR spectrum of 2-methyl-7,12,17-tri(methoxyethyl)porphycene, CDCl$_3$, 80 MHz, δ (ppm)=3.12 (wide singlet) N$\underline{H}$; 3.6 (singlet, 12H) $\underline{H}_3$COCH$_2$ and H$_3$C at C-2); 4.36 (singlet, 12H) MeO$\underline{C}$H$_2$CH$_2$; 9.25 (singlet, 1H), 9.34 (3 singlets, 3H) H at $\overline{C\text{-}3}$, $\overline{6}$, 13, 16; 9.68, 9.71 (2 singlets, 4H) H at C-9, 10, 19, 20.

Mass spectrum of 2-methyl-7,12,17-tri(methoxyethyl)porphycene, EI, 75 eV: m/z=498 (M+, 78%); 453 (M—MeOCH$_2$+, 100%); 408 (M—2MeOCH$_2$+, 26%).

9-Acetoxy-2,7,12,17-tetrakis (methoxyethyl)porphycene

A solution of 542 mg (1 mmol) 2,7,12,17-tetrakis(methoxyethyl)porphycene in 75 ml CH$_2$CL$_2$ freshly distilled over LiAlH$_4$, and 75 ml glacial acetic acid was combined with 179 mg (0.75 mmol) PbO$_2$ and stirred for 20 min. at room temperature. The reaction mixture was then poured into 500 ml water and extracted with 250 ml dichloromethane. After washing the organic phase once with concentrated aqueous sodium hydrogen carbonate (150 ml) and twice with water (200 ml), the organic layer was evaporated under vacuum. The residue was chromatographed with dichloromethane/ethylacetate (1:1) on silica gel (column 40×5 cm). The first eluted compound consisted of unchanged tetrakis(methoxyethyl)-porphycene (195 mg). Following evaporation of the solvent and crystallization the second, largest fraction from methanol/water, the title compound 9-acetoxy-tetrakis(methoxyethyl)porphycene was obtained in the form of small, violet needles having a melting point of 107° C. Yield: 153 mg, 40%

Mass spectrum, EI, 70 eV, m/z=600 (M+, 87%); 558 ([M—CH$_2$CO]+, 100%); 557 ([M—CH$_3$CO]+, 22%); 513 ([M—MeOCH$_2$—CH$_2$CO]+, 36%).

UV/VIS spectrum, CH$_2$Cl$_2$, λmax[nm] (ε)=370 (1.39×10$^5$); 382 (9.1×10$^4$); 562 (2.9×10$^4$); 604 (3.2×10$^4$); 633 (3.2×10$^4$); 640 (3.0×10$^4$).

IR spectrum, CsI pellet, ν (cm$^{-1}$) 2924, 2872 (C—H), 1758 (C=O), 1115 (C—O), 1458, 1074, 1002, 816.

Solubility of the title compound in selected solvents: Excellent: ethyl acetate, THF, CHCl$_3$, CH$_2$Cl$_2$; Good:

DMSO, DEET, DMF, Toluene, acetone; Moderate: EtOH, MeOH, i-propanol; Insoluble: hexane, water.

2,7-Bis(methoxyethyl)-12,17-di-n-propylporphycene

A stirred suspension under protective gas of 17.4 g (260 mmol) zinc powder and 1.7 g (16.8 mmol) anhydrous CuCl in 700 ml of THF freshly distilled over LiAlH$_4$ was mixed in 30 minutes dropwise with 14.2 ml (130 mmol) TiCl$_4$. Subsequently the mixture was heated under reflux for three hours. At this stage, a solution of 1.36 g (5 mmol) 5,5'-diformyl-4,4'-di-n-propyl-2,2'-bipyrrole and 1.52 g (5 mmol) 5,5'-diformyl-4,4'-bis(methoxyethyl)-2,2'-bipyrrole in 300 ml THF, was added, with stirring, within 45 minutes to the black McMurry reagent. The reaction was stirred for two minutes at the boiling temperature of the tetrahydrofuran and then cooled to 0° C. A this temperature 250 ml of 10% NH$_3$ solution were added dropwise over one hour. The reaction mixture was treated with 500 ml THF, stirred under oxygen for 90 minutes and filtered off. The residue was extracted with 200 ml of CH$_2$Cl$_2$ and the combined organic layers were evaporated under vacuum. The residue, which contained black polymers, was dissolved as thoroughly as possible in dichloromethane and filtered over Celite. The black residue was ground up and extracted with further dichloromethane. The combined organic phases were evaporated under vacuum and the dark blue residue was taken up into CH$_2$Cl$_2$ and placed on an alumina column. (Brockmann, II—III activity, column 10×5 cm). All the blue, red fluorescing fractions were collected and rechromatographed with CH$_2$Cl$_2$/ethyl acetate (100:4) on silica gel (column 25×5 cm). The first eluted compound consisted of tetra-n-propylporphycene, followed by the main compound bis(methoxyethyl)-di-n-propylporphycene. The third fraction was the tetrakis(methoxyethyl)porphycene, eluted with ethyl acetate. After dividing those three fractions, it was necessary to further remove small quantities of minor compounds by recrystallization. The first fraction with tetra-n-propylporphycene was recrystallized after evaporation of the solvent from dichloromethane/hexane.

By evaporation of the solvent and recrystallization of the second fraction from CH$_2$Cl$_2$/MeOH, the title compound bis(methoxyethyl)-di-n-propylporphycene was obtained in the form of long, violet, metallically glistening needles having a melting point of 142° C. The porphycene-tetraether (third fraction) was purified by recrystallization from CH$_2$Cl$_2$/MeOH.

| Total yield of three porphycenes: | 22% (560 mg; 1.10 mmol) |
|---|---|
| 2,7-bis(methoxyethyl)-12,17-di-n-propylporphycene: | 11% (280 mg; 0.55 mmol) |
| 2,7,12,17-tetrakis(methoxyethyl)-porphycene: | 5.5% (146 mg; 0.27 mmol) |
| 2,7,12,17-tetra-n-propylporphycene: | 5.5% (134 mg; 0.28 mmol) |

$^1$H-NMR spectrum of bis(methoxyethyl)-di-n-propylporphycene, CDCl$_3$, 300 MHz, δ (ppm)=1.34 (triplet, 6H) —CH$_2$CH$_2$CH$_3$; 2.41 (multiplet, 4H) —CH$_2$CH$_2$CH$_3$; 3.14 (wide singlet, 2H) NH; 3.59 (singlet, 6H) —CH$_2$CH$_2$OCH$_3$; 4.00 (triplet, 4H) —CH$_2$CH$_2$CH$_3$; 4.31 (singlet, 8H) —CH$_2$CH$_2$OCH$_3$; 9.27 (singlet, 2H) H-13, H-16; 9.34 (singlet, 2H) H-3, H-6; 9.71 (singlet, 4H) H-9, H-10, H-19, H-20.

$^{13}$C-NMR spectrum, CDCl$_3$, 75.5 MHz, δ (ppm)=14.51 (—CH$_2$CH$_2$CH$_3$); 25.22 (—CH$_2$CH$_2$CH$_3$); 28.89 (—CH$_2$CH$_2$OCH$_3$); 30.45 (—CH$_2$CH$_2$CH$_3$); 58.99 (—CH$_2$CH$_2$OCH$_3$); 74.09 (—CH$_2$CH$_2$OCH$_3$); 110.52 (C-9, C-10, C-19, C-20); 122.88 (C-13, C-16); 123.42 (C-6); 134.16 (C-4, C-5); 134.22 (C-14, C-15); 140.65 (C-2, C-7); 143.34 (C-11, C-18); 143.82 (C-1, C-8); 145.01 (C-12, C-17).

Mass spectrum, EI, 70 eV, m/z=510 (M+, 100%); 481 ([M—C$_2$H$_5$.]+, 13%); 466 ([M—C$_3$H$_8$.]+, 31%); 466 ([M—MeOCH$_2$.]+, 88%); 420([M—2MeOCH$_2$.]+, 32%); 255 (M$^{2+}$, 4%).

UV/VIS spectrum, CH$_2$Cl$_2$, δ max[nm] (ε)=370 (142000); 382 (100000); 562 (36000); 601 (34000); 633 (49000).

IR spectrum, CsI pellet, ν (cm$^{-1}$) 2955, 2927, 2868 (C—H); 1116 (C—O); 1458, 1214, 1083, 1018, 816.

2,7,12,17-Tetrakis(methoxyethyl)porphycenatonickel (II)

A suspension of 380 mg (0.7 mmol) tetrakis(methoxyethyl)porphycene in 120 mL of acetic acid was heated with reflux with 1.7 g (7 mmol) Ni(OAc)$_2$·4H$_2$O for five hours. The reaction can be followed by means of thin layer chromatography (CH$_2$Cl$_2$/ethyl acetate (4:1), silica gel). In so doing, the nickel complex appears as a less mobile, blue fraction without fluorescence. Following complete complexing, the mixture was poured into 600 mL of water and extracted three times with 150 mL CHCl$_3$. The combined organic phases were washed twice with water and a saturated NaHCO$_3$ solution and again twice with water, then dried over MgSO$_4$ and the solvent evaporated under vacuum. 398 mg (0.67 mmol) bluish-violet, matted needles of the title compound having a melting point of 182° C. was obtained from the residue through recrystallization from CH$_2$Cl$_2$/MeOH. The yield was 95%.

If the raw product of (9) obtained following the first chromatography is added, a mixture of partially degraded porphycenes can be separated in the form of its nickel complex even at this stage by means of chromatography on silica gel (column 4×40 cm) with CH$_2$Cl$_2$/ethyl acetate (3:1).

1H-NMR spectrum of the title compound, CDCl$_3$, 300 MHz, δ (ppm)=3.58 singlet, 12H) H$_3$COCH$_2$; 4.20 (A$_2$B$_2$ system, 16H) MeOCH$_2$CH$_2$; 8.82 (singlet, 4H) H at C-3, 6, 13, 16; 9.28 (singlet, 4H) H at C-9, 10, 19, 20.

Mass spectrum, DEI, 75 eV; m/z=599 (M+, 15%); 554 (M—MeOCH$_2$+, 8%).

IR spectrum, CsI pellet, ν (cm$^{-1}$) 2887, 2870, 2810 (CH), 1117 (C-0, ether), 1489, 974, 839, 812.

UV/VIS spectrum CH$_2$Cl$_2$, λmax[nm] (ε)=265 (3.1×10$^4$); 387 (1.27×10$^5$); 603 (6.3×10$^4$).

Bis-, tris-, and tetrakis(bromoethyl)porphycenes 120 mg (0.2 mmol) tetrakis(methoxyethyl)porphycenatonickel (II) were dissolved under protective gas in 150 mL of CH$_2$Cl$_2$ freshly distilled over LiAlH$_4$ and treated with 100 mg (1.6 mmol) boric acid. The reaction was cooled to −78° C. and 100 mg (75 μL, 0.8 mmol) BBr$_3$ were added at one time under cooling and in the dark. Cooling the boron tribromide to −20° C. facilitates its handling. The reaction was thawed over ten hours and then 100 mL of 5% NaHCO$_3$ solution were added at 0° C. within 30 minutes while stirring vigorously. Another 200 mL of CH$_2$Cl$_2$ are added and the organic phase was separated out. This was washed twice, each time with a saturated NaHCO$_3$ solution and water and dried over MgSO$_4$. The solvent was evaporated under vacuum and the residue was dried at 0.1 torr.

The blue solid obtained was treated with 20 mL of 98% $H_2SO_4$ and stirred for 30 minutes. The resulting blue, red fluorescing solution was poured into 1.2 L of deionized water and extracted four times with 150 mL of $CHCl_3$. The combined organic phases were washed with water and a 5% sodium hydrogen carbonate solution and the solvent was removed under vacuum. The residue was chromatographed twice with chloroform on silica gel (column 2×30 cm). From the first blue fraction of the second chromatography, 29 mg (0.04 mmol) of 2,7,12,17 tetrakis(bromoethyl)porphycene were obtained by means of crystallization from $CHCl_3$ in the form of small, violet needles, which did not exhibit a melting point until 300° C. The yield was 20%.

A similar procedure can be applied to the three isomeric bis(bromoethyl)bis(methoxyethyl)porphycenes and 2,7,12-tris(bromoethyl)-17-(methoxyethyl)porphycene. In the case of bis(bromoethyl)bis(methoxyethyl)-porphycenes, 30 mg (0.48 mmol) boric acid and 60 mg (0.24 mmol) $BBr_3$ were used for 120 mg (0.2 mmol) of the nickel complex. To isolate the tris(bromoethyl) compound, 50 mg (0.8 mmol) $B(OH)_3$ and 100 mg (0.4 mmol) $BBr_3$ were added to the same quantity of the nickel complex. The yield was 25% and 30%, respectively. The tris (bromoethyl) porphycene begins to decompose at 250° C., becoming black, without exhibiting a melting point until 300° C. when heated rapidly.

Mass spectrum of 2,7,12,17-tetrakis(bromoethyl)porphycenatonickel (II), EI, 75 eV: m/z=794/96 (M+, 3%); 704/06 (M-Br+, 58%); 467/69 (M-4Br+, 30%).

$^1$H-NMR spectrum of 2,7,12,17tetrakis(bromoethyl) porphycene (TBEP), $D_2SO_4$, 80 MHz, δ (ppm)=4.32 and 4.53 (2 triplets, 16H) $BrCH_2CH_2$; 10.16 (singlet, 4H) H at 9, 10, 19, 20.

IR spectrum of (TBEP), CsI pellet, ν (cm$^{-1}$)=2958, 2920 (CH), 1261, 1046, 799.

UV/VIS spectrum of (TBEP), $CH_2Cl_2$, λmax[nm] (ε)=369 (1.02×10$^5$); 383 (7.9×10$^4$); 564 (2.5×10$^4$); 605 (2.9×10$^4$); 637 (3.2×10$^4$.)

$^1$H-NMR spectrum of bis(bromoethyl)bis(methoxyethyl)porphycene (mixture of isomers), $CDCl_3$, 80 MHz, δ (ppm)=3.20 (wide singlet) NH; 3.61 (singlet, 6H) $H_3COCH_2$; 4.33 (singlet, 8H) $MeOCH_2CH_2$; 4.26, 4.50, 4.59 (3 multiplets, 8H) $BrCH_2CH_2$; 9.37 (multiplet, 4H) H at C-3, 6, 13, 16; 9.76, 9.66 (3 multiplets, 4H) H at C-9, 10, 19, 20.

$^1$H-NMR spectrum of 2,7,12-tris(bromoethyl)-17-methoxyethylporphycene, $CDCl_3$, 80 MHz, δ (ppm)=3.11 (wide singlet) NH; 3.61 (singlet, 3H) $H_3COCH_2$; 4.19, 4.58 (2 multiplets, 12H) $BrCH_2CH_2$; 4.32 (singlet, 4H) $MeOCH_2CH_2$; 9.34, 9.35 (2 singlets, 4H) H at C-3, 6, 13, 16; 9.62, 9.67, 9.68 (3 singlets, 4H) H at C-9, 10, 19, 20.

Mass spectrum, EI, 75 eV; m/z=497 (M-2Br—MeOH+, 2%); 94/96 ($CH_3Br+$, 100%).

IR spectrum, CsI pellet, ν (cm$^{-1}$) 2962, 2925 (CH), 1140 (C-0, ether), 963, 816.

2,7,12,17-Tetravinylporphycene

At room temperature while stirring in the dark, 243 mg (248 μL, 1.6 mmol) DBU were added all at once to a solution of 14.8 mg (20 μmol) tetrakis(bromoethyl)porphycene in 50 mL of absolute THF. After thirty minutes, the agitator was turned off and the mixture left to stand at room temperature for two days. Subsequently the greenish-blue solution was treated with 80 mL of $CH_2Cl_2$ and poured into 80 mL of 0.5% HCl. The organic phase was shaken out and washed with water and a 2% $NaHCO_3$ solution, dried over $Na_2SO_4$ and the solvent was evaporated under vacuum. The residue was chromatographed with $CH_2Cl_2$ on aluminum oxide (Brockmann, II–III activity stage, column 2×10 cm) and the first green fraction was collected. The solvent was slowly evaporated under a slight vacuum and the remaining fine crystalline solid was washed with 3 mL of ice cooled, absolute pentane. Following drying under a high vacuum, 4.1 mg (10 μmol) tetravinylporphycene were obtained. The title compound decomposed even with traces of oxygen in the presence of light. The yield was 50%.

All reagents and solvents were purged of oxygen by introducing inert gas and all purification steps were carried out under subdued light, as was the reaction.

$^1$H-NMR spectrum of, $CD_2Cl_2$, 300 MHz, δ (ppm)=3.64 (wide singlet) NH; 6.01 (doublet of doublets, 4H) CH=$CH_2$-cis$^3$Jcis=11.0 Hz; 6.68 (doublet of doublets, 4H) CH=$CH_2$-trans$^3$Jcis=17.4 Hz; 8.31 (doublet of doublets, 4H) $CH$=$CH_2$; 9.68 (singlet, 4H) H at C-3, 6, 13, 16; 9.86 (singlet, 4H) H at C-9, 10, 19, 20.

UV/VIS spectrum, $CH_2Cl_2$, λmax[nm] (ε)=383 (3.2×10$^4$); 597 (1.1×10$^4$); 642 (1.5×10$^4$); 676 (1.3×10$^4$).

2-Bromoethyl-7,12,17-tris(methoxyethyl)porphyceneatonickel (II)

A solution of 419 mg (0.7 mmol) tetrakis(methoxyethyl)porphycenatonickel complex in 250 mL of $CH_2Cl_2$ freshly distilled over $LiAlH_4$ was treated with 62 mg (1 mmol) boric acid and 126 mg (48 μL, 0.5 mmol) $BBr_3$ were added all at once under protective gas at −78° C. The mixture was left to thaw over eight hours and 50 mL of 5% $NaHCO_3$ solution were added dropwise over 10 minutes at 0° C. The organic phase was separated off and washed sequentially with a saturated $NaHCO_3$ solution and water. Following drying over $MgSO_4$, the solvent was evaporated under vacuum and purified by means of chromatography on silica gel (column 4×40 cm, $CH_2Cl_2$/ethyl acetate/methanol (80:20:1)). The first three fractions contained various ether-split nickel porphycenes; the 2-bromoethyl-7,12,17-tris(methoxyethyl)porphycenato-nickel (II) was eluted as the fourth fraction. Following removal of the solvent and recrystallization from $CH_2Cl_2$/methanol there resulted 159 mg (0.245 mmol, yield 35%, reaction yield 70%) of bluish-violet crystals having a melting point of 186°–189° C. The fifth blue band yielded after evaporation of the solvent and crystallization 209 mg (0.35 mmol) of the educt, 2,7,12,17-tetrakis(methoxyethyl)-porphycenato-nickel (II).

$^1$H-NMR spectrum, $CDCl_3$, 300 MHz, δ (ppm)=3.58, 3.59 (2 singlets, 9H) $H_3COCH_2$; 4.06, 4.10 (2 multiplets, 16 H) $MeOCH_2CH_2$ and $BrCH_2CH_2$; 8.34, 8.45 (2 singlets, 2H) H at C-3, 6; 8.55, 8.57 (2 singlets, 2H) H at C-13, 16; 8.70 ($A_2B_2$ system, 2H) H at C-19, 20; 8.95 (singlet, 2H) H at C-9, 10.

$^{13}$C-NMR spectrum, $CDCl_3$, 75.5 MHz, δ (ppm)=29.1 ($CH_2CH_2OMe$; 32.3, 32.4 ($CH_2CH_2Br$); 59.0 ($CH_2OCH_3$); 73.7 ($CH_2CH_2OMe$); 106.6, 106.8, 107.0, 107.2, (C-9, 10, 19, 20); 119.1, 119.4, 119.5, 119.6 (C-3, 6, 13, 16); 145.1, 144.1, 143.8, 142.6, 146.6 (C-4, 5, 14, 15, 1, 2, 7, 8, 11, 12, 17, 18).

IR spectrum, CsI pellet, ν (cm$^{-1}$)=2920, 2870 (CH) 1116 (C-0, ether), 1618, 1560, 1488, 974, 811.

Mass spectrum, EI, 75 eV: m/z=648 (M+, 45%); 603 (M—$MeOCH_2$+, 54%); 432 (M-3$MeOCH_2$—Br+, 18%); 418 (M-3MeOCH$_2$-CH$_2$Br+, 21%); 94 (CH$_3$Br+, 35%); 80 (HBr+, 100%).

UV/VIS spectrum, CH$_2$Cl$_2$, λmax[nm] (ε)=264 (3.2×10$^4$); 387 (1.28×10$^5$); 605 (6.5×10$^4$).

2-Bromoethyl-7,12,17-tris(methoxyethyl)porphycene

To demetallate, 97.2 mg (0.15 mmol) of the above-described bromoethylporphycenatonickel complex were suspended in 12 mL of concentrated sulfuric acid and stirred for ten minutes until a clear solution was produced. The reaction solution was poured in 1 L of water and extracted three times with 150 mL of CHCl$_3$. The combined organic phases were washed three times with water and once with a 1% NaHCO$_3$ solution and dried over MgSO$_4$. Following evaporation of the solvent under vacuum and recrystallization from CH$_2$Cl$_2$/MeOH, 80 mg (0.135 mmol) of the title compound were obtained in the form of long, violet, metallically glistening needles with a melting point of 164° C. Yield: 90 percent.

Elementary analysis: calc. C 62.94% H 5.96% N 9.47% Br 13.51% found C 62.87% H 5.87% N 9.55% Br 13.56%

$^1$H-NMR spectrum, CF$_3$CO$_2$D, 300 MHz, δ (ppm)=3.83, 3.84 (2 singlets, 9H) H$_3$COC$\underline{H}_2$; 4.27 (triplet, 2 H) BrC$\underline{H}_2$CH$_2$; 4.56, 4.66 (2 multiplets, 14H) MeOC$\underline{H}_2$CH$_2$ and BrCH$_2$C$\underline{H}_2$; 10.03 (multiplet 4H) H at C-3, 6, 13, 16; 10.54 (multiplet, 4H) H at C-9, 10, 19, 20.

$^{13}$C-NMR spectrum, CDCl$_3$, 75.5 MHz, δ (ppm)=28.85 (MeOCH$_2$$\underline{C}$H$_2$); 32.2, 32.9 (Br$\underline{C}$H$_2$CH$_2$); 59.0 (H$_3$$\underline{C}$OCH$_3$); 73.9 (MeO$\underline{C}$H$_2$CH$_2$); 110.5, 110.8, 110.9, 111.1, (C-9, 10, 19, 20); 123.5, 123.6, 123.9, 124.0 (C-3, 6, 13, 16); 133.5, 134.1, 134.2, 135.0 (C-4, 5, 14, 15); 140.58, 140.61, 140.9, 141.0, 142.9, 143.0, 144.5, (C-1, 2, 7, 8, 11, 12, 17, 18).

IR spectrum, CsI pellet, ν (cm$^{-1}$)=2908, 2860 (CH) 1116 (C-0, ether), 1558, 1208, 937, 814.

Mass spectrum, EI, 75 eV; m/z=592 (M+, 8%); 547 (M—MeOCH$_2$+, 2%); 511 (M—Br+, 1%).

UV/VIS spectrum, CH$_2$Cl$_2$, λmax[nm] (ε)=243 (1.3×10$^4$); 370 (1.33×10$^5$); 832 (9.5×10$^4$); 564 (3.4×10$^4$); 546 (3.4×10$^4$); 603 (3.2×10$^4$); 635 (4.5×10$^4$).

2-Vinyl-7,12,17-tris(methoxyethyl)porphycene

All of the reagents and solvents used in the following procedure were purged of oxygen by introducing inert gas and all of the purification steps were carried out, as in the reaction itself, under subdued light.

71 mg (0.12 mmol) of 2-bromoethyl-7,12,17tris(methoxyethyl)porphycene were dissolved in 50 mL of absolute THF and treated with 1.8 g (1.86 ml, 12 mmol) DBU under protective gas. The reaction solution was stirred at 40° C. for 90 minutes in the dark and subsequently treated with 150 mL of absolute dichloromethane. The mixture was poured into 100 mL of 5% hydrochloric acid, neutralized by shaking with a 2% NaHCO$_3$ solution and then washed with water. The organic phase obtained was separated off and evaporated under a slight vacuum. The residue was chromatographed with CH$_2$Cl$_2$ on aluminum oxide (Brockmann, activity stage II–III, column 3×10 cm). Following crystallization from dichloro-methane and drying under oil pump vacuum, 52.6 mg (0.103 mmol) of the title compound were obtained from the single mobile blue fraction as needle-shaped crystals having a melting point of 119°–120° C. (with decomposition). Yield: 86%.

$^1$H-NMR spectrum, CDCL$_3$, 300 MHz, δ (ppm)=3.05 (wide singlet) N$\underline{H}$; 3.59, 3.95, 3.40 (3 singlets, 9H) H$_3$COC$\underline{H}_2$; 4.28 (multiplet, 12H) MeOC$\underline{H}_2$C$\underline{H}_2$; 5.95 (doublet of doublets, 1H) C$\underline{H}$=CH$_2$ cis; 6.60 (doublet of doublets, 1H) CH=C$\underline{H}_2$ trans; 8.25 (doublet of doublets) CH=CH$_2$; 9.25, 9.26 (2 singlets, 3H) H at C-3, 6, 13, 16; 9.53 (singlet, 1H) H at C-3; 9.60 (AB system, 2H) H at C-9, 10; 9.69 (AB system, 2H) H at C-19, 20.

Mass spectrum, FAb, 75 eV; m/z=510 (M+, 100%); 465 (M—MeOCH$_2$+, 23 %).

IR spectrum, CsI pellet: ν (cm$^{-1}$) 2968, 2922, 2870 (CH), 1116 (C-0, ether), 1727, 1557, 1460, 1440, 801.

UV/VIS spectrum, CH$_2$Cl$_2$, λmax[nm] (ε)=373 (9.8×10$^4$); 572 (2.6×10$^4$); 613 (2.8×10$^4$); 643 (3.3×10$^4$).

Cleavage of 2,7,12,17-tetrakis(methoxyethyl)porphycene with BBr$_3$

The following procedure was carried out in a totally dry and oxygen free atmosphere with especially dried equipment and solvents.

70 μL (0.74 mmol) freshly distilled boron tribromide in 70 mL of dichloromethane were added during 60 minutes to a vigorously stirred solution of 542 mg (1 mmol) tetrakis(methoxyethyl)porphycene in 150 mL of the same solvent at −30° C. Over the next 16 hours, the mixture was allowed to reach room temperature and 25 mL of a 8% aqueous solution of sodium hydrogen carbonate were added in one portion. The precipitate was filtrated off by the aid of Celite ®, washed with sodium hydrogen carbonate solution and with water. The collected solids were extracted with methanol. The dichloromethane phase of the filtrate was extracted once with sodium hyarogen carbonate solution, twice with water and then combined with the methanol extract. The raw product mixture was preadsorbed by evaporating the organic phase on addition of 15 g of alumina, and fractionated on a column of silica gel (2×60 cm) with dichloromethane/ethyl acetate/ethanol (100:10:1). After a forerun of 300-360 mg (50–65% depending on the extent of remaining water in solvent and equipment) unchanged starting material (tetrakis(methoxyethyl)-porphycene), the 2-hydroxyethyl-7,12,17-tris(methoxyethyl)porphycene was eluted, which was then crystallized from toluene/hexane (1:1) to afford 17–18% (93 mg) of dark violet cubes melting at 131° C. By the use of chloroform/methanol (8:1) the isomeric bis(hydroxyethyl)bis(methoxyethyl)porphycenes as well as the tris(hydroxyethyl)mono(methoxyethyl)porphycene were eluted, which could be obtained in 10–12% (53 mg) and 4% (20 mg) yield, respectively.

2-Hydroxyethl-7,12,17-tris(methoxyethyl)porphycene

Mass spectrum: (75 eV)m/z=528 (80%; M+·); 497(10%; [M—HOCH$_2$·]+); 483 (100%; [M—CH$_3$OCH$_2$·]+).

IR spectrum: (CsI): ν (cm$^{-1}$) 3462 (OH); 2921; 2869; 1561; 1460; 1405; 1215; 1115 (ether); 1017; 968; 884; 815.

UV/VIS spectrum: (dichloromethane) λ$_{max}$[nm] (ε)=370 (134000); 563 (33600); 602 (31200); 635 (43900).

2,12-Bis(hydroxyethyl)-7,17-bis(methoxyethyl)porphycene (3rd fraction)

Mass spectrum: (75 eV) m/z=514 (90%; M+); 483 (40%; [M—HOCH$_2$·]+); 469 (100%; [M—CH$_3$OCH$_2$·]+).

¹H-NMR spectrum: (80 MHz, DMSO-d6) δ (ppm)=9.92 (singlet 4 H) H-9, H-10, H-19, H-20; 9.67 (singlet 4 H) H-3, H-6, H-13, H-16; 5.12 (triplet 2H)—OH; 4.31 (multiplet 8 H) HOCH$_2$CH$_2$; 4.30 (singlet 8 H) H$_3$COCH$_2$CH$_2$; 3.50 (singlet 6 H) H$_3$CO—; 3.09 (wide singlet 2 H) NH.

IR spectrum: (CsI) ν (cm$^{-1}$)=3424 (OH); 2912 (CH); 1870; 1560; 1459; 1415; 1388; 1216; 1108; 1064; 1013; 974; 889; 815; 625; 522.

UV/VIS spectrum: (DMSO) λ$_{max}$[nm]=251 (10000); 309 (12300); 371 (130000); 383 (92800); 530 (5600) (sh); 554 (22600) (sh); 562 (31900); 601 (32100); 632 (44400).

2,7-Bis(hydroxyethyl-12,17-bis(methoxyethyl)porphycene and
2,17-Bis(hydroxyethyl-7,12-bis(methoxyethyl)porphycene (4th fraction)

Mass spectrum: (75 eV) m/z=514 (100%; M+), 483 (40%; [M—HOCH$_2$·]+); 469 (100%; [M—CH$_3$OCH$_2$·]+).

¹H-NMR spectrum: (80 MHz, DMSO-d6) δ (ppm)=9.94 (singlet; 4 H) H-9, H-10, H-19, H-20; 9.68 (singlet; 4 H) H-3, H-6, H-13, H-16; 5.73 (triplet; 2 H) —OH; 4.32 (multiplet; 8 H) HOCH$_2$CH$_2$; 4.31 (singlet; 8 H) H$_3$COCH$_2$CH$_2$; 3.50 (singlet; 6 H) —OCH$_3$; 3.09 (wide singlet; 2H) NH.

IR spectrum: (CsI) ν (cm$^{-1}$)=2877 (CH); 1851; 1654; 1560; 1459; 1380; 1215; 1116; 1050; 1007; 887; 815; 626, 522.

UV/VIS spectrum: (DMSO) λ$_{max}$[nm] (ε)=262 (8000); 310 (13000); 370 (136700); 383 (99000); 529 (5800) (sh); 551 (20800) (sh); 562 (34200); 601 (34600); 632 (48000).

2,7,12-Tris(hydroxyethyl)-17-methoxyethylporphycene

Mass spectrum: (75 eV) m/z=500 (100%; M+·); 469 (70%; [M—HOCH$_2$·]+); 455 (75%; [M—CH$_3$OCH$_2$·]+).

IR spectrum: (CsI) ν (cm$^{-1}$)=3331 (OH); 2870 (CH); 1870; 1460; 1371; 1220; 1046; 1008; 967; 886; 816; 626; 518.

UV/VIS spectrum: (DMSO) λ$_{max}$[nm] (ε)=370 (134000); 382 (97000); 563 (33600); 602 (31200); 635 (43900).

2,7,12,17-Tetrakis(acetoxyethyl)porphycene

At −30° C. and in an atmosphere of argon a solution of 108.4 mg (0.2 mmol) tetrakis (methoxyethyl) porphycene in 100 ml freshly dried dichloromethane was treated with 0.2 ml (2.1 mmol) pure boron tribromide. The solution was stirred for 16 hours, quenched with 10 ml of dilute ammonia and the precipitate was separated, washed with dichloromethane, water and ether and dried in vacuo. The crude 2,7,12,17-tetrakis(hydroxyethyl)porphycene was dissolved in 25 ml pyridine and 5 ml acetic anhydride stirred for 16 hours, evaporated and washed with water. The residue was chromatographed with dichloromethane/acetone (40:1) on silica gel (2×15 cm). The second blue fraction contained 66 mg (50%) of the title compound, which after recrystallization from benzene yielded violet needles melting at 188°–189° C.

Mass spectrum: (75 eV) m/z=654 (100%; M+·); 594 (35%; [M—CH$_3$CO$_2$H]+·); 581 (15%; [M—CH$_3$CO$_2$CH$_2$·]+); 534 (35%; [M—2CH$_3$CO$_2$H]+·).

1H-NMR spectrum: (80 MHz, CDCl$_3$) δ (ppm)=9.67 (singlet; 4 H) H-9, H-10, H-19, H-20; 9.29 (singlet; 4H) H-3, H-6, H-13, H-16; 4.99 (AX-System ³J(H-3a, H-3b)=7.0 Hz; 8 H) H-2a, H-7a, H-12a, H-17a; 4.34 (AX-System; 8H) H-2b, H-7b, H-12b, H-17b; 3.06 (wide singlet; 2H) NH; 2.14 (singlet, 12 H)—OAc.

IR spectrum: (CsI) ν (cm$^{-1}$)=2955 (CH); 1733 (C=O); 1465; 1373; 1238; 1027 (C—O—ester); 965; 887; 806; 608; 517; 478.

US/VIS spectrum: (dichloromethane) λ$_{max}$[nm] (ε)=242 (14000); 369 (144000); 381 (103000); 564 (37000); 603 (35000); 635 (50000).

2,7,12,17-Tetrakis(hydroxyethyl)porphycene 32.7 mg (50 μmol) Tetrakis(acetoxyethyl)porphycene were dissolved in 20 ml of dry tetrahydrofuran and 27 mg (0.5 mmol) sodium methoxide in 1 ml absolute methanol was added. The solution was allowed to stand without agitation while the pure tetrakis(hydroxyethyl)porphycene crystallized as small violet needles, which did not melt below 350° C. (yield: 22 mg=90%).

Mass spectrum: (75 eV) m/z=486 (50%; M+·); 455 (80%; [M—HOCH$_2$.]+); 425 (30%; [M—HOCH$_2$.—OCH$_2$]+); 393 (25%; [M—3HOCH$_2$.]+).

IR spectrum: (CsI) ν (cm$^{-1}$)=3328 (OH); 2895; 1463; 1372; 1220; 1043 (C—O); 880; 824; 396.

UV/VIS spectrum: (DMSO) λ$_{max}$[nm] (ε)=372 (92400); 385 (83000); 570 (26200); 611 (20400); 647 (28300).

2-Chloroethyl-7,12,17-tris(methoxyethylporphycene 39.6 mg (75 μmol) 2-Hydroxyethyl-7,12,17-tris(methoxyethyl)porphycene were dissolved in 10 ml dimethylformamide (free from water and amine) and at 0° C. 2 ml (27.5 mmol) of purified thionylchloride were added quickly. The solution warmed up and was directly poured into 100 ml dilute aqueous ammonia. The ammonia was extracted three times with trichloromethane, and the combined organic phases were then washed five times with water. After evaporation of the solvents the crude product was chromatographed on silica gel (2×80 cm) with trichloromethane/ethyl acetate (20:1; third blue fraction) and repeatedly recrystallized from dichloromethane/hexane and washed with ether and hexane. This procedure gave 4.1 mg (10%) chloroethylporphycene as tiny violet needles.

Mass spectrum: (70 eV) m/z=546/548 (45%; M+·); 512 (90%; [M+H.—Cl.]+·); 501/503 (55%; [M—CH$_3$OCH$_2$.]+; 482 (15%; [M—CH$_3$O.—Cl.]+·); 467 (100%; [M+H—CH$_3$OCH$_2$.—Cl.]+).

¹H-NMR spectrum: (80 MHz, CDCl$_3$) δ (ppm)=9.69 (singlet; 2 H) H-9, H-10; 9.63 (A$_2$B$_2$-System; 2 H) H-19, H-20; 9.30 (singlet; 4 H) H-3, H-6, H-13, H-16; 4.42 (A$_2$B$_2$-System; 4 H) H-2a, H-2b; 4.30 (singlet; 12 H) H-7a, H-7b, H-12a, H-12b, H-17a, H-17b; 3.60 (singlet; 12H)—OCH$_3$; 3.04 (broad singlet; 2 H)—NH.

IR spectrum: (CsI) ν (cm$^{-1}$)=2984 (CH); 2903 (CH); 2808 (CH); 1121 (CO); 1846; 1560; 1458; 1420; 1391; 1263; 1214; 1066; 1019; 999; 969; 885; 819; 768; 692; 652; 553; 520; 497.

Methanesulfonate of 2-hydroxyethyl-7,12,17-tris(methoxyethyl)porphycene

To a well-stirred solution of 52.8 mg (0.1 mmol) 2-hydroxyethyl-7,12,17-tris(methoxyethyl)porphycene in 100 ml dichloromethane and 9 ml pyridine were added during one hour 8.1 ml (1.05 mmol) methanesulfonylchloride. After another hour the solution was poured onto 200 ml ice chilled water, the organic phase was separated and the aqueous phase was extracted twice with dichloromethane. The combined organic phases were washed five times with water, the solvents were evaporated and the resulting blue oil was chromatographed thrice with trichloromethane/ethyl acetate (20:1) on silicagel (2×20cm). The content of the blue fractions were recrystallized from dichloromethane/petrol to yield 55 mg (91%) of violet at 145° C. melting crystals.

Mass spectrum: (75 eV)=m/z=606 (2%; M+.); 562 (2%; [M—CH$_3$OCH$_2$.]+); 512 (10%; [M—CH$_2$SO$_2$OCH$_2$.]+); 467 (13%; [M—CH$_2$SO$_2$O—CH$_3$OCH$_2$.]+); 96 (80%; CH$_2$SO$_2$O+.); 79 (100%; CH$_3$SO$_2$+.).

IR spectrum: (CsI) $\nu$ (cm$^{-1}$)=2978 (CH); 2869 (CH); 1357 (S=O); 1176 (S—O); 1114 (C—O); 1852; 1560; 1460; 1390; 1215; 1069; 1019; 973; 886; 816; 728; 649; 626; 556; 528; 508.

UT/VIS spectrum: (dichloromethane) $\lambda_{max}$[nm] ($\epsilon$)=242 (13400); 310 (12300); 369 (141000); 381 (104000); 532 (6200); 563 (35700); 603 (34100); 635 (48400).

2,3,4,6Tetra-O-acetyl-$\beta$-D-galactopyranoside of 2-hydroxyethyl-7,12,17-tris(methoxyethyl)-porphycene 1 g of dry, freshly prepared silver carbonate and 1 g anhydrous sodium sulfate were added to a solution of 42.2 mg (0.08 mmol) 2-hydroxyethyl-7,12,17-tris(methoxyethyl)porphycene and 658 mg 2,3,4,6-tetra-O-acetyl-$\alpha$-D-galactopyranosyl bromide in 50 ml of anhydrous dichloromethane, and the mixture was stirred in the dark with rigorous protection from moisture until thin layer chromatography (tlc) (silica gel: dichloromethane/methanol, 20:1) indicated the disappearance of educt (about 3 days). The reaction mixture was filtered through a pad of Celite, and the inorganic solids were washed with dichloromethane.

The filtrate and washings were combined, washed with water, dried (sodium sulfate) and evaporated to give a syrup which was fractionated by repeated recrystallization from ethanol and finally ether/pentane. This procedure yielded 6.9 mg 910%) of violet cubes melting at 95° C.

Mass spectrum: (75 eV) m/z=858 (100%; M+.); 814 (45%; [M—CH$_2$CO]+.); 511 (10%; [M—C$_6$H$_5$O(OAc)$_4$O.]+); 497 (10%; [M—C$_6$H$_5$O(OAc)$_4$OCH$_2$.]+); 375 (5%; [M—C$_6$H$_5$O(OAc)$_4$O—3CH$_3$OCH$_2$.]+.); (80%; CH$_3$CO+.).

IR spectrum: (CsI) $\nu$ (cm$^{-1}$)=2932 (CH); 1752; (C=O); 1560; 1460; 1371; 1227; 1114; 1057; 966; 888; 814; 602; 536.

UV/VIS spectrum: (dichloromethane) $\lambda_{max}$[nm] ($\epsilon$)=242 (13100); 309 (12300); 369 (140000); 382 (100000); 532 (6000) (sh); 563 (35100); 602 (33500); 634 (47500).

$\beta$-D-Galactopyranoside of 2-hydroxyethyl-7,12,17-tris(methoxyethyl)porphycene A solution of 17.2 mg (0.02 mmol) of the tetra-O-acetyl-compound (the mother liquors of the previous reaction could also be used) in 10 ml absolute tetrahydrofuran was treated with methanolic 0.05 M sodium methoxide (40 ml). The solution was kept for 2 hours at room temperature, and 10 ml brine was added was well as 20 ml water. The organic phase was separated, the aqueous phase was extracted twice was 20 ml tetrahydrofuran and the combined extracts were washed thrice with dilute aqueous sodium chloride, dried (sodium sulfate) and evaporated. The resulting residue was recrystallized from methanol to yield, after washing with water and cold ether small violet needles. m.p.=124° C.

IR spectrum: (CsI) $\nu$ (cm$^{-1}$)=3417 (OH); 2926 (CH); 1116 (C—O); 1561; 1461; 1383; 1218; 1018; 966; 888; 816; 626; 529.

UV/VIS spectrum: (ethanol) $\lambda_{max}$[nm] ($\epsilon$)=373 (125800); 384 (103900) (sh); 572 (33500); 613 (37400); 645 (44700).

2-Cyanoethyl-7,12,17-tris(methoxyethyl)porphycene 202 mg (0.33 mmol) methanesulfonate or 197 mg (0.33 mmol) monobromoethyl porphycene were dissolved in 120 ml dry dimethylsulfoxide, and sodium cyanide (491 mg/10 mmol, dried for 16 hours at 110° C.) was added. The suspension was stirred in the dark under an atmosphere of argon until no more educt could be detected (tlc, silica gel: dichloromethane/acetone, 40:1, 3 hours). The dimethylsulfoxide was distilled off at an maximum bath temperature of 50° C., and the residue was taken up in 300 ml trichloromethane and washed with three 100 ml portions of water. After drying and evaporating the solvent the resulting product was fractionated on a column (3×30 cm) of silica gel eluting with dichloromethane/ethyl acetate (15:1). When the bromo compound is used as the starting material, protection from light is advisable.

The second blue fraction afforded after recrystallization from benzene 135 mg (75%) in the case of the methanesulfonate as starting material, and 104 mg (58%) in the case of reacting with the bromide, of blue violet needles of the nitrile; m.p. 166°-167° C.

Mass spectrum: (70 eV) m/z=537 (60%, M+.); 492 (100%, [M—CH$_3$OH]+.); 452 (4%, [M—CH$_3$OCH$_2$.]+); 447 (10%, [M—2CH$_3$OCH$_2$.]+); 407 (20%, [M—NCCH$_2$—2CH$_3$OCH$_2$.]+); 402 (15%, [M—3CH$_3$OCH$_2$.]+); 362 (10%, [M—NCCH$_2$.—CH$_3$OCH$_2$.]+).

IR spectrum: (CsI) $\nu$ (cm$^{-1}$)=2920; 2900 (CH); 2243 (CN); 1846; 1215; 1119 (C—O).

UV/VIS spectrum: (dichloromethane) $\lambda_{max}$[nm] ($\epsilon$)=370 (115000); 382 (86700); 564 (29000); 603 (28700); 635 (40400).

2,7,12-Tris(methoxyethyl)-17-methoxypropionylporphycene

A suspension of 53.7 mg (0.1 mmol) cyanoethylporphycene in 15 ml anhydrous methanol was saturated at 0° C. with dry hydrogen chloride, so that the porphycene was completely dissolved and then stirred for 18 hours under protection from light. The now green solution was added to 100 g ice, neutralized with aqueous 5N sodium hydroxide and the precipitate was extracted with 200 ml dichloromethane. The solution was washed with water, dried, the solvent was evaporated and the product was purified by chromatography with 8:1 dichloromethane/acetone (1.5×10 cm) followed by recrystallization from benzene/hexane to afford 46.1 mg (81%) of violet needles, which melted at 137°-139° C.

Mass spectrum: (70 eV) m/z=570 (80%, M+); 525 (100%, [M—CH$_3$OCH$_2$.]+); 480 (20%, [M—2CH$_3$OCH$_2$.]+.).

IR spectrum: (CsI) $\nu$ (cm$^{-1}$)=2870 (CH); 1849; 1736 (C=O); 1562; 1458; 1389; 1361; 1213; 1116 (C—O—ester); 1067 (C—O—ether); 1018; 998; 968; 882; 812; 710; 546; 364.

UV/VIS spectrum: (dichloromethane) $\lambda_{max}$[nm] ($\epsilon$)=370 (146000); 382 (105000); 563 (37200); 602 (35500); 634 (50700).

2-carboxyethyl-7,12,17-tris(methoxyethyl)porphycene

A solution of 45.6 mg (80 μmol), 2,7,12-tris(methoxyethyl)-17-methoxypropionylporphycene in 15 ml tetrahydrofuran was treated with 10 ml aqueous potassium hydroxide (2N) and stirred for 40 hours in the dark. The precipitate was separated from the nearly colorless solution, washed successively with water and dichloromethane and taken up in a mixture of dichloromethane and 1N hydrochloric acid. The dichloromethane phase was twice washed with 0.5N hydrochloric acid, dried over magnesium sulfate, and evaporated to give 29 mg (72%) of a microcrystalline powder.

Mass spectrum: (75 eV) m/z=556 (60%; M+.); 511 (100%, [M—CHO$_2$.]+; [M—CH$_3$OCH$_2$.]+); 466 (25%, [M—2CH$_3$OCH$_2$.]+; [M—CHO$_2$.—CH$_3$OCH$_2$.]+); 421 (25%, [M—CO$_2$H.—2CH$_3$OCH$_2$.]+); 407 (10%, [M—CH$_2$CO$_2$H.—2CH$_3$OCH$_2$.]+); 375 (10%, [M—CO$_2$H.—3$CH_3OCH_2$.]+.).

$^1$H-NMR spectrum: (80 MHz, CF$_3$COOD) δ (ppm)=10.61 (wide singlet, 4 H) C-9, C-10, C-19, C-20; 10.09 (multiplet, 4 H) C-3, C-13, C-16; 4.67 (multiplet; 16 H) C-2a, C-2b, C-7a, C-7b, C-12a, C-12b, C-17a, C-17b; 3.91 (singlet, 9H) —OCH.

IR spectrum: (CsI) ν (cm$^{-1}$)=3444 (OH); 2922 (C—H); 1710 (C=O); 1562; 1459; 1208; 1117 (C—O); 1016; 964; 883; 812.

UV/VIS spectrum: (dichloromethane/4% trifluoroacetic acid) λ$_{max}$[nm] (ε)=370 (120000); 382 (90000); 562 (30000); 602 (28000); 634 (41000).

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A porphycene having the structure

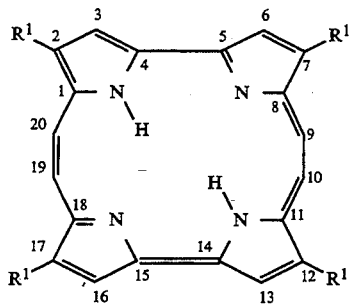

wherein each R$^1$ is, independently, (a) —(CH$_2$)$_n$-X where X is an amino acid, oligopeptide covalently bonded by an ether-, ester- or amine-bond or where X is —Y—(CH$_2$)$_n$-porphycene$^2$, where porphycene$^2$ is a compound of the same said structure, n=1-4 and Y is a direct bond; —O—; or —CH=CH—; or (b) where one, two or three of the substituents R$^1$ are C$_{1-6}$ alkyl or C$_{6-20}$ carbocyclic aryl and the remaining substituents are as above under (a) and pharmaceutically acceptable salts and metal complexes thereof.

2. A pharmaceutical composition comprising the porphycene of claim 1 and a pharmaceutically acceptable carrier or diluent.

3. The pharmaceutical composition of claim 2, wherein said composition is a solution of said porphycene in water, water-alcohol or dimethyl sulfoxide.

4. A method of photodynamic therapy, comprising the steps of:
   administering to a mammal in need thereof, an effective amount or, the porphycene of claim 1, and
   irradiating said mammal with light at a wavelength in the absorption spectrum of said porphycene.

5. The method of claim 4, wherein said administering is topical administration.

6. The method of claim 4, wherein said administering is enteral, parenteral or intramuscular administration.

7. A method of purifying or decontaminating a fluid, comprising
   contacting said fluid with the porphycene of claim 1, and
   irradiating said fluid in contact with the porphycene with light at a wavelength in the absorption spectrum of said porphycene.

8. The method of claim 7, wherein said fluid is blood.

9. The method of claim 7, wherein said porphycene is covalently bonded to a stationary supports.

10. The compound 9-acetoxy-2,7,12,17-tetrakis(methoxyethyl)porphycene.

11. A method of photodynamic therapy, comprising the steps of:
    administering to a mammal in need thereof, an effective amount of the porphycene of claim 10, and
    irradiating said mammal with light at a wavelength in the absorption spectrum of said porphycene.

12. The porphycene of claim 1, wherein X is a naturally occurring amino acid.

13. The porphycene of claim 1, wherein X is an oligopeptide having 2-6 amino acid residues.

14. The porphycene of claim 13, wherein X is an oligopeptide having 2-3 amino acid residues.

15. A porphycene having the structure

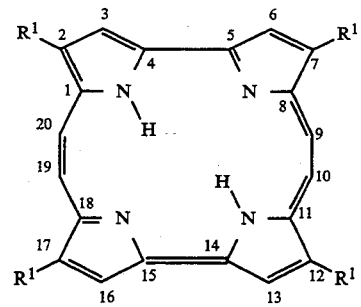

wherein each R$^1$ is, independently, (a) —(CH$_2$)$_n$-X where X is an amino acid, oligopeptide covalently bonded by an ether-, ester- or amine-bond or where X is —Y—(CH$_2$)$_n$-porphycene$^2$, where porphycene$^2$ is a compound of the same said structure, n=1-4 and Y is a direct bond; —O—; or —CH=CH—; or (b) wherein 1, 2, or 3 of the substituents R$^1$ are C$_{1-6}$ alkyl and the remaining substituents are as above under (a).

* * * * *

UNITED STATES PATENT AND TRADEMARK OFFICE
CERTIFICATE OF CORRECTION

PATENT NO. : 5,409,900  
DATED : April 25, 1995  
INVENTOR(S) : Emanuel Vogel, et al Page 1 of 2

It is certified that error appears in the above-indentified patent and that said Letters Patent is hereby corrected as shown below:

In the drawings:

Figure 1, far left-hand side, 1st chemical formula, change " " to -- --; 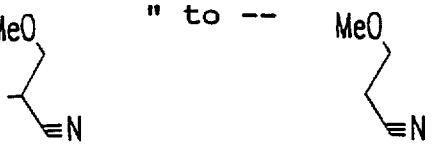

far left-hand margin, in the formula of compound (3) (third row of chemical formulas), change the substituent "1" to --CO$_2$H--;

in the third row of chemical formulas, going from compound (2) to compound (3), step 1, change "AcOH.HCO$_2$H" to --AcOH, HCO$_2$H--.

Figure 2, first row, below the formula on the far right-hand side, change "ISOMERE" to --ISOMERS--.

Figure 3:
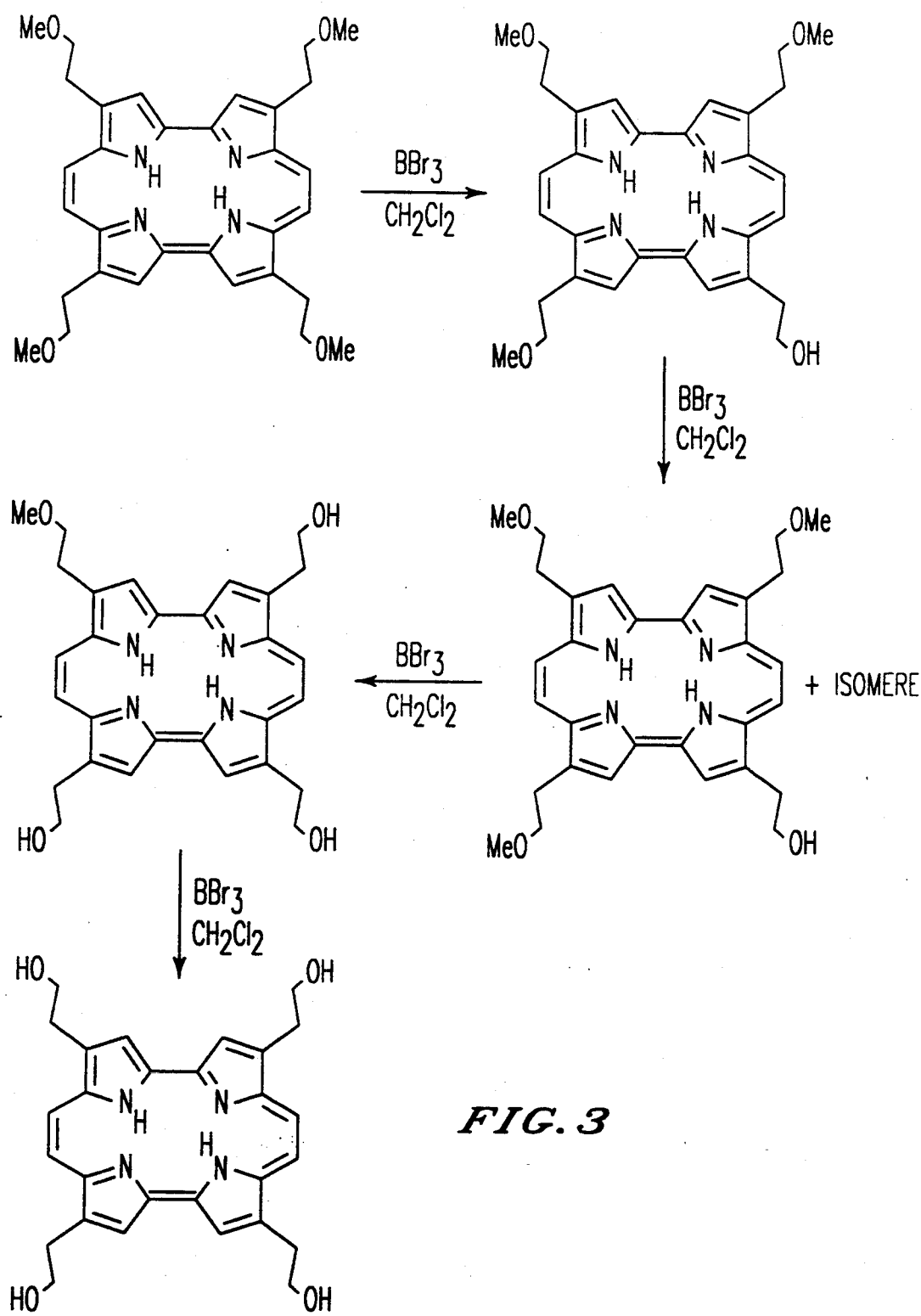
FIG. 3 illustrates the preparation of mono-, bis-, tris and tetrakis(hydroxyalkyl)porphycene compounds of the present invention.
Figure 4:
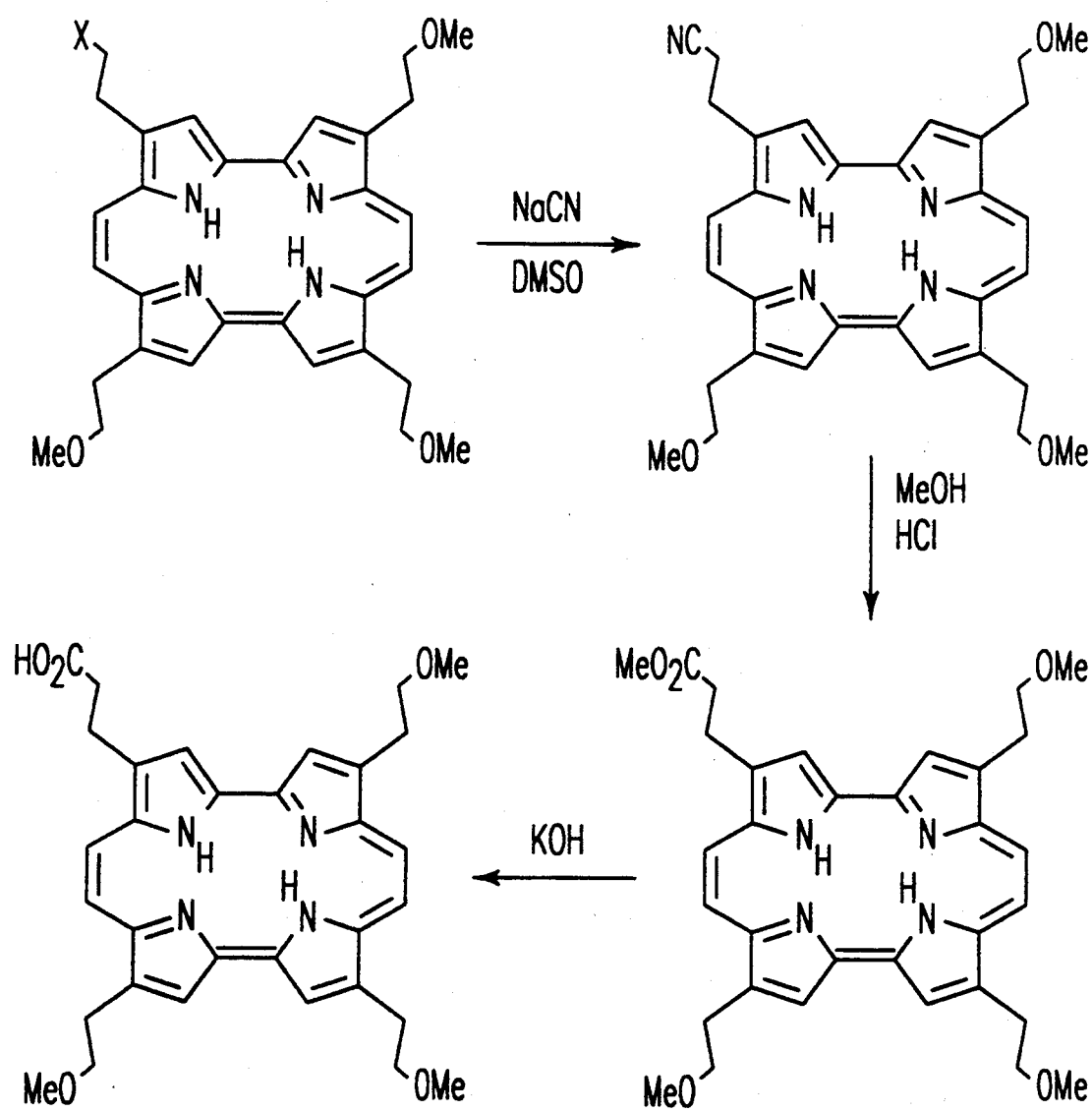
FIG. 4 illustrates the preparation of porphycene carboxylic acid compounds of the present invention.

Figure 3, second row of chemical formulas, right-hand formula, change "MeO" (lower left-hand occurrence) to --HO--, and change "ISOMERE" to --ISOMERS--.

Column 5, line 60, delete "-".

Column 6, line 9, before the chemical formula, insert -- + --;

UNITED STATES PATENT AND TRADEMARK OFFICE
CERTIFICATE OF CORRECTION

PATENT NO.  : 5,409,900
DATED       : April 25, 1995
INVENTOR(S) : Emanuel Vogel, et al It is certified that error appears in the above-indentified patent and that said Letters Patent is hereby corrected as shown below:

line 24, before the chemical formula, insert -- + --, and delete "-".

Column 14, line 36, change "wall" to --membrane--.

Signed and Sealed this

Fourteenth Day of November, 1995

Attest:

BRUCE LEHMAN

Attesting Officer

Commissioner of Patents and Trademarks